(12) United States Patent
Jansen et al.

(10) Patent No.: US 10,189,764 B2
(45) Date of Patent: *Jan. 29, 2019

(54) HYDROGENATION OF OXYGENATED MOLECULES FROM BIOMASS REFINING

(71) Applicant: Virdia, Inc., Raceland, LA (US)

(72) Inventors: Robert Jansen, Collinsville, IL (US); Noa Lapidot, Mevaseret Zion (IL); James Alan Lawson, Ellsworth, ME (US); Michael Zviely, Haifa (IL); Neta Matis, Hod Hasharon (IL); Lee Madsen, Danville, VA (US); Bassem Hallac, Jerusalem (IL); Philip Travisano, Danville, VA (US)

(73) Assignee: VIRDIA, INC., Raceland, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/883,894

(22) Filed: Jan. 30, 2018

(65) Prior Publication Data

US 2019/0002381 A1 Jan. 3, 2019

Related U.S. Application Data

(63) Continuation of application No. 15/304,790, filed as application No. PCT/US2015/030431 on May 12, 2015, now Pat. No. 9,926,252.

(60) Provisional application No. 61/992,131, filed on May 12, 2014.

(51) Int. Cl.

| C07C 45/00 | (2006.01) |
|---|---|
| C07C 29/00 | (2006.01) |
| C01B 3/00 | (2006.01) |
| C07D 307/08 | (2006.01) |
| C07C 29/17 | (2006.01) |
| C07C 5/03 | (2006.01) |
| C01B 3/22 | (2006.01) |

(52) U.S. Cl.
CPC ............ *C07C 45/002* (2013.01); *C01B 3/22* (2013.01); *C07C 5/03* (2013.01); *C07C 29/172* (2013.01); *C07C 29/175* (2013.01); *C07D 307/08* (2013.01); *C01B 2203/047* (2013.01); *C01B 2203/0475* (2013.01); *C01B 2203/1047* (2013.01); *C01B 2203/1058* (2013.01); *C01B 2203/1064* (2013.01); *C01B 2203/1076* (2013.01); *C01B 2203/1211* (2013.01); *C01B 2203/1217* (2013.01); *C07C 2523/44* (2013.01); *C07C 2523/72* (2013.01); *C07C 2523/86* (2013.01)

(58) Field of Classification Search
CPC ....... C07C 45/002; C07C 29/172; C01B 3/22; C01B 2203/1217

See application file for complete search history.

(56) References Cited

U.S. PATENT DOCUMENTS

| 2,400,959 A | 5/1946 | Stewart |
|---|---|---|
| 2,829,165 A | 4/1958 | Coussemant |
| 3,070,633 A | 12/1962 | Utne et al. |
| 3,083,236 A | 3/1963 | Utne et al. |
| 4,304,843 A | 12/1981 | Manger et al. |
| 4,400,468 A | 8/1983 | Faber |
| 7,015,359 B1 | 3/2006 | Rao et al. |
| 7,994,347 B2 | 8/2011 | Lilga et al. |
| 8,367,851 B2 | 2/2013 | Lilga et al. |
| 8,501,989 B2 | 8/2013 | Boussie et al. |
| 8,669,397 B2 | 3/2014 | Boussie et al. |
| 8,742,144 B2 | 6/2014 | Lilga et al. |
| 8,846,984 B2 | 9/2014 | Allgeier et al. |
| 8,846,985 B2 | 9/2014 | Allgeier et al. |
| 8,853,458 B2 | 10/2014 | Dias et al. |
| 8,859,826 B2 | 10/2014 | Allgeier et al. |
| 8,865,940 B2 | 10/2014 | Allgeier et al. |
| 8,884,035 B2 | 11/2014 | DeSilva et al. |
| 8,889,912 B2 | 11/2014 | Allgeier et al. |
| 8,889,922 B2 | 11/2014 | Allgeier et al. |
| 8,962,894 B2 | 2/2015 | Allgeier et al. |
| 9,926,252 B2 | 3/2018 | Jansen et al. |
| 2007/0287845 A1 | 12/2007 | Lilga et al. |
| 2010/0137665 A1 | 6/2010 | Chen |
| 2010/0317822 A1 | 12/2010 | Boussie et al. |
| 2010/0317823 A1 | 12/2010 | Boussie et al. |
| 2011/0046423 A1 | 2/2011 | Sughrue et al. |
| 2011/0257419 A1 | 10/2011 | Lilga et al. |
| 2011/0306780 A1 | 12/2011 | Lilga et al. |
| 2013/0137863 A1 | 5/2013 | De Vries et al. |
| 2013/0172578 A1 | 7/2013 | Allgeier et al. |
| 2013/0172586 A1 | 7/2013 | Desilva et al. |
| 2013/0172629 A1 | 7/2013 | Allgeier et al. |
| 2013/0184495 A1 | 7/2013 | Dias et al. |
| 2013/0231505 A1 | 9/2013 | Allgeier et al. |
| 2013/0289311 A1 | 10/2013 | Allgeier et al. |
| 2013/0289312 A1 | 10/2013 | Allgeier et al. |
| 2013/0289318 A1 | 10/2013 | Allgeier et al. |
| 2013/0289319 A1 | 10/2013 | Allgeier et al. |
| 2014/0228596 A1 | 8/2014 | Allgeier et al. |

FOREIGN PATENT DOCUMENTS

| WO | WO-2007146836 A1 | 12/2007 |
|---|---|---|
| WO | WO-2010015081 A1 | 2/2010 |
| WO | WO-2011149339 A1 | 12/2011 |
| WO | WO-2011155964 A1 | 12/2011 |
| WO | WO-2013101969 A1 | 7/2013 |
| WO | WO-2013101970 A1 | 7/2013 |
| WO | WO-2013101980 A1 | 7/2013 |
| WO | WO-2013109477 A1 | 7/2013 |

(Continued)

OTHER PUBLICATIONS

Notice of Allowance dated Nov. 17, 2017 for U.S. Appl. No. 15/304,790.

(Continued)

*Primary Examiner* — Sikarl A Witherspoon

(74) *Attorney, Agent, or Firm* — Wilson Sonsini Goodrich & Rosati

(57) ABSTRACT

The present disclosure relates to methods, processes, and systems for utilizing the dehydrogenation of 2-butanol for hydrogen consuming reactions of biomass or biomass-derived molecules.

30 Claims, 6 Drawing Sheets

(56) References Cited

FOREIGN PATENT DOCUMENTS

| WO | WO-2013163540 A1 | 10/2013 |
|----|------------------|---------|
| WO | WO-2013163547 A1 | 10/2013 |
| WO | WO-2013163556 A1 | 10/2013 |
| WO | WO-2013163561 A1 | 10/2013 |
| WO | WO-2015175571 A1 | 11/2015 |

OTHER PUBLICATIONS

Office Action dated Jun. 6, 2017 for U.S. Appl. No. 15/304,790.
Alamillo, et al. The selective hydrogenation of biomass-derived 5-hydroxymethylfurfural using heterogeneous catalysts. Green Chem. 2012; 14:1413-1419.
Buntara, et al. Caprolactam from Renewable Resources: Catalytic Conversion of 5-Hydroxymethylfurfural into Caprolactone. Angewandte Chemie International Edition. Jul. 25, 2011; 50(31):7083-7087.
European Search Report and Search Opinion dated Dec. 15, 2017 for European Patent Application No. EP15792589.2.
Hintermair, et al. Hydrogen-transfer catalysis with Cp*Ir3 complexes: the influence of the ancillary ligands. ACS Catal. 2014; 4:99-108.
International search report and written opinion dated Sep. 21, 2015 for PCT/US2015/030431.
Panagiotopoulou, et al. Effect of hydrogen donor on liquid phase catalytic transfer hydrogenation of furfural over a Ru/RuO2/C catalyst. Journal of Molecular Catalysis A Chemical. 2014; 392:223-228.
Tuteja, et al. Direct Synthesis of 1,6-Hexanediol from HMF over a Heterogeneous Pd/ZrP Catalyst using Formic Acid as Hydrogen Source. ChemSusChem. 2014; 7: 96-100.
Upare, et al. An integrated process for the production of 2,5-dimethylfuran from fructose. Green Chem. 2015; 17:3310-3313.
Werkmeister, et al. Selective Ruthenium-Catalyzed Transfer Hydrogenations of Nitriles to Amines with 2-Butanol. Chemistry—A European Journal. Apr. 2, 2013; 19(14):4437-4440.
West et al. Catalytic conversion of biomass-derived carbohydrates to fuels and chemicals by formation and upgrading of monofunctional hydrocarbon intermediates. Catalysis Today. vol. 147, Issue 2, 30 Sep. 2009, pp. 115-125.
Xu, et al. Direct catalytic conversion of furfural to 1,5-pentanediol by hydrogenolysis of the furan ring under mild conditions over Pt/Co2AlO4 catalyst. Chem Commun (CAMB). Apr. 7, 2011;47(13):3924-6. doi: 10.1039/c0cc05775d. Epub Feb. 23, 2011.
Yao, et al. One-Step Conversion of Biomass-Derived 5-Hydroxymethylfurfural to 1,2,6-Hexanetriol Over Ni—Co—Al Mixed Oxide Catalysts Under Mild Conditions. ACS Sustainable Chem. Eng. 2014; 2(2):173-180.

HYDROGENATION OF OXYGENATED MOLECULES FROM BIOMASS REFINING

CROSS-REFERENCE

This application is a Continuation of U.S. application Ser. No. 15/304,790, filed Oct. 17, 2016, which is a National Stage Entry of PCT/US2015/030431, filed May 12, 2015, which claims the benefit of U.S. Provisional Application No. 61/992,131, filed May 12, 2014, each of which is incorporated herein by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

FIELD OF THE INVENTION

The invention relates to the hydrogenation, hydrogenolysis, and hydrodeoxygenation of biomass derived molecules.

BACKGROUND OF THE INVENTION

Industrial chemicals obtained from inexpensive sources are desirable for use in industrial processes, for example, as raw materials, solvents, or starting materials. It has become increasingly desirable to obtain industrial chemicals, or their precursors, from materials that are not only inexpensive but that are also more environmentally friendly. Of particular interest are materials that can be obtained from renewable sources, such as materials that are produced by a biological activity such as planting, farming, or harvesting.

SUMMARY OF THE INVENTION

The present invention relates to methods, processes, and systems for utilizing the dehydrogenation of 2-butanol for hydrogen consuming hydrogenation, hydrogenolysis, or hydrodeoxygenation reactions of biomass or biomass-derived molecules.

Provided herein are methods for using 2-butanol as the hydrogen source for a conversion reaction. The methods can comprise: dehydrogenating 2-butanol to yield 2-butanone; wherein hydrogen removed from the 2-butanol during dehydrogenating is the hydrogen source for the conversion reaction; and wherein the conversion reaction can comprise hydrogenation, hydrogenolysis, or hydrodeoxygenation. In the methods disclosed herein, the conversion reaction can convert a biomass-derived molecule to form a product. In the methods disclosed herein, the biomass-derived molecule can be derived from lignocellulosic biomass, and the biomass-derived molecule can be selected from a saccharide, a dehydrated saccharide, a halodehydrated saccharide, a dehydrated and partially hydrogenated saccharide, or a hydrogenated saccharide, or a combination thereof. In the methods disclosed herein, the saccharide or the dehydrated saccharide can be selected from monosaccharide, oligosaccharide, furfural, halofurfural, methyl furfural, furfuryl alcohol, methyl furfuryl alcohol, (methoxymethyl)-methyl furfural, hydroxymethylfurfural, 2-methylfuran, dimethylfuran, 2,5-bis(hydroxymethyl)furan, 5-hydroxymethyl-2-[(1-methylethoxy)methyl] furan, and 2-methyl-5[(1-methylmethoxy) methyl] furan, bis(1-methoxyethyxy)-methyl furan, tetrahydrofuran, or levoglucosenone, or a combination thereof. In the methods disclosed herein, the dehydrated and partially hydrogenated saccharide can be selected from 1,2,6-hexanetriol, 1,2,5-pentanetriol, 1,2,4-butanetriol, 2,4-dihydroxy butanoic acid, or succinic acid, malic acid, maleic acid, or a combination thereof. In the methods disclosed herein, the hydrogenated saccharide can be selected from xylitol, mannitol, sorbitol, erythritol, arabitol, or galactitol, or a combination thereof. In the methods disclosed herein, the weight yield of the product can be at least 40%, 45%, 50%, 55%, 60%, 65%, 70%, 75%, 80%, 85%, or 90%. In the methods disclosed herein, the selectivity to the product can be at least 40%, 45%, 50%, 55%, 60%, 65%, 70%, 75%, 80%, 85%, or 90%.

In the methods disclosed herein, the method can comprise diluting 2-butanol with a solvent, wherein the solvent can be inert in the conversion reaction. In the methods disclosed herein, the solvent can comprise a $C_4$-$C_{18}$ hydrocarbon. In the methods disclosed herein, the $C_4$-$C_{18}$ hydrocarbon can be selected from hexane, cyclohexane, heptane, octane, decane, dodecane, or a combination thereof. In the methods disclosed herein, the method can further comprise catalyzing the dehydrogenation reaction and the conversion reaction with a catalyst. In the methods disclosed herein, catalyzing can be achieved using a copper-based catalyst, a Raney nickel-based catalyst, a metal containing organosilica-based catalyst, or an iridium complex-based catalyst, or a combination thereof. In the methods disclosed herein, catalyzing can be achieved using a co-catalyst, an enhancer, or a promoter, or a combination thereof. In the methods disclosed herein, the dehydrogenation reaction and the conversion reaction can occur in one reaction vessel; or the dehydrogenation reaction and the conversion reaction can occur in more than one reactor vessels, wherein the more than one reactor vessels are functionally connected either continuously or discontinuously.

In the methods disclosed herein, the conversion reaction can comprise conversion of furfural to 1,5-pentanediol. In the methods disclosed herein, the conversion of furfural to 1,5-pentanediol can comprise: contacting furfural with the hydrogen removed from the 2-butanol during dehydrogenation in the presence of a first catalyst at a first temperature and a first pressure to yield furfuryl alcohol; and contacting furfuryl alcohol with the hydrogen removed from the 2-butanol during dehydrogenation in the presence of a second catalyst at a second temperature and a second pressure to yield 1,5-pentanediol; wherein the first catalyst and the second catalyst, the first temperature and the second temperature, and the first pressure and the second pressure are the same or different; and wherein the dehydrogenation reaction and the conversion reaction occur in one reaction vessel, or wherein the dehydrogenation reaction and the conversion reaction occur in more than one reactor vessels, wherein the more than one reactor vessels are functionally connected either continuously or discontinuously. In the methods disclosed herein, the first catalyst can be xCu-yMgO-zCr$_2$O$_3$, where x, y, and z are the amounts in terms of weight percent of Cu, MgO, and Cr$_2$O$_3$, respectively. In the methods disclosed herein, the conversion of furfural to 1,5-pentanediol can be achieved using a co-catalyst, an enhancer, or a promoter. In the methods disclosed herein, the first temperature can be less than 100, 110, 120, 130, 140, 150, 160, 170, 180, 190, 200, 210, 220, 230, 250, or 250° C. In the methods disclosed herein, the molar ratio of 2-butanol to furfural can be 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.0, 9.5, or 10.0.

In the methods disclosed herein, the conversion reaction can comprise conversion of hydroxymethylfurfural to 1,6-hexanediol. In the methods disclosed herein, the conversion of hydroxymethylfurfural to 1,6-hexanediol can comprise: contacting hydroxymethylfurfural with the hydrogen removed from the 2-butanol during dehydrogenation in the presence of a first catalyst at a first temperature and a first pressure to yield bi-hydrodroxymethyl furan; contacting bi-hydrodroxymethyl furan with the hydrogen removed from the 2-butanol during dehydrogenation in the presence of a second catalyst at a second temperature and a second pressure to yield hexanetriol; contacting hexanetriol with the hydrogen removed from the 2-butanol during dehydrogenation in the presence of a third catalyst at a third temperature and a third pressure to yield 1,6-hexanediol; wherein the first catalyst, the second catalyst, and the third catalyst; the first temperature, the second temperature, and the third temperature; and the first pressure, the second pressure, and the third pressure are the same or different; and wherein the dehydrogenation reaction and the conversion reaction occur in one reaction vessel, or wherein the dehydrogenation reaction and the conversion reaction occur in more than one reactor vessels, wherein the more than one reactor vessels are functionally connected either or discontinuously. In the methods disclosed herein, at least 40%, 45%, 50%, 55%, 60%, 65%, 70%, 75%, 80%, 85%, or 90% of converted hydroxymethylfurfural can be converted to 1,6-hexanediol. In the methods disclosed herein, the first catalyst can comprise a metal-containing organosilica catalyst comprising one or more metal catalyst or a precursor thereof and silica, wherein the metal catalyst or a precursor thereof is incorporated into a network of Si—O—Si bonds of the silica. In the methods disclosed herein, the catalyst can comprise one or more metal catalyst or a precursor thereof and can comprise Cu, CuO, $Cu_2Cr_2O_5$, Pd, PdO, Pt, Rh, Ru, Co, Fe, or Ag, or a combination thereof. In the methods disclosed herein, the conversion of hydroxymethylfurfural to 1,6-hexanediol can be achieved using a co-catalyst, an enhancer, or a promoter, or a combination thereof. In the methods disclosed herein, the method can further comprise processing 1,6-hexanediol to produce a commercial product. In the methods disclosed herein, the commercial product can comprise a polymer, wherein the polymer can be selected from polyester, polyurethane, polyamide, polycarbonate, polyacetate or epoxy resin, or a combination thereof.

In the methods disclosed herein, the conversion reaction can comprise conversion of 2,4-hydroxybutanoic acid to 1,4-butanediol. In the methods disclosed herein, the conversion of 2,4-hydroxybutanoic acid to 1,4-butanediol can comprise: contacting 2,4-hydroxybutanoic acid with the hydrogen removed from the 2-butanol during dehydrogenation in the presence of a first catalyst at a first temperature and a first pressure to yield 1,2,4-butanetriol; and contacting 1,2,4-butanetriol with the hydrogen removed from the 2-butanol during dehydrogenation in the presence of a second catalyst at a second temperature and a second pressure to yield 1,4-butanediol; wherein the first catalyst and the second catalyst, the first temperature and the second temperature, and the first pressure and the second pressure are the same or different; and wherein the dehydrogenation reaction and the conversion reaction occur in one reaction vessel, or wherein the dehydrogenation reaction and the conversion reaction occur in more than one reactor vessels, wherein the more than one reactor vessels are functionally connected either continuously or discontinuously. In the methods disclosed herein, the conversion of 2,4-hydroxybutanoic acid to 1,4-butanediol can be achieved using a co-catalyst, an enhancer, or a promoter, or a combination thereof. In the methods disclosed herein, at least 40%, 45%, 50%, 55%, 60%, 65%, 70%, 75%, 80%, 85%, 90%, or 95% of 2-butanol can be dehydrogenated. In the methods disclosed herein, the percent weight yield of MEK from dehydrogenated 2-butanol can be at least 65%, 70%, 75%, 80%, 85%, 90%, or 95%. In the methods disclosed herein, the method can not comprise adding formic acid, isopropanol, or gaseous molecular hydrogen from a source other than the hydrogen removed from the 2-butanol during dehydrogenation. In the methods disclosed herein, the conversion reaction can convert a biomass-derived molecule to form a product.

Provided herein are processes to convert a biomass-derived molecule to a conversion product. The processes can comprise: using the conversion reaction to convert the biomass-derived molecule to the conversion product; wherein the conversion reaction can comprise hydrogenation, hydrogenolysis, or hydrodeoxygenation; and using a dehydrogenation reaction as a source of hydrogen for the conversion reaction. In the processes disclosed herein, the dehydrogenation reaction can comprise dehydrogenation of 2-butanol to 2-butanone. In the processes disclosed herein, at least 40%, 45%, 50%, 55%, 60%, 65%, 70%, 75%, 80%, 85%, 90%, or 95% of 2-butanol can be dehydrogenated. In the processes disclosed herein, the percent weight yield of MEK from dehydrogenated 2-butanol can be at least 65%, 70%, 75%, 80%, 85%, 90%, or 95%.

In the processes disclosed herein, the processes can further comprise diluting 2-butanol with a solvent, wherein the solvent can be inert in the conversion reaction. In the processes disclosed herein, the solvent can comprise a $C_4$-$C_{18}$ hydrocarbon. In the processes disclosed herein, the $C_4$-$C_{18}$ hydrocarbon can be selected from hexane, cyclohexane, heptane, octane, decane, or dodecane, or a combination thereof. In the processes disclosed herein, the process can further comprise catalyzing the dehydrogenation reaction and the conversion reaction with a catalyst. In the processes disclosed herein, catalyzing can be achieved using a copper-based catalyst, a Raney nickel-based catalyst, a metal containing organosilica-based catalyst, or an iridium complex-based catalyst, or a combination thereof. In the processes disclosed herein, catalyzing can be achieved using a co-catalyst, an enhancer, or a promoter, or a combination thereof. In the processes disclosed herein, the dehydrogenation reaction and the conversion reaction can occur in one reaction vessel; or the dehydrogenation reaction and the conversion reaction can occur in more than one reactor vessels, wherein the more than one reactor vessels are functionally connected either continuously or discontinuously. In the processes disclosed herein, the conversion reaction can be performed under an inert gas. In the processes disclosed herein, the inert gas can be nitrogen. In the processes disclosed herein, the conversion reaction can be performed under pressure. In the processes disclosed herein, the conversion reaction can be performed under a pressure of 50, 100, 200, 300, 400, 500, 600, 700, 800, 900, 1000, 1100, or 1200 psi. In the processes disclosed herein, the conversion reaction can be performed at a temperature of 50, 60, 70, 80, 90, 100, 110, 120, 130, 140, 150, 160, 170, 180, 190, 200, 210, 220, 230, 240, 250, 260, 270, 280, 290, or 300° C. In the processes disclosed herein, the conversion reaction can be performed for a time period of 0.1, 0.5, 1, 2, 3, 4, 5, 6, 7, 8, 9, 10, 11, 12, 13, 14, 15, 16, 17, 18, 19, 20, 21, 22, 23, or 24 hours.

In the processes disclosed herein, the biomass-derived molecule can be derived from lignocellulosic biomass. In the processes disclosed herein, the product can comprise at least 50 ppb, 60 ppb, 70 ppb, 80 ppb, 90 ppb, 100 ppb, 110 ppb, 120 ppb, 130 ppb, 140 ppb, or 150 ppb of a marker molecule, and wherein the marker molecule can be selected from 2-butanol, 2-butanone, 5-[(1-methylpropoxy)methyl]-2-furancarboxaldehyde, 5-hydroxymethyl-2-[(1-methylpropoxy) methyl] furan, 2-methyl-5-[(1-methylpropoxy) methyl]furan, or 2,5-[bis(1-methylpropoxy)-methyl] furan, or a combination thereof.

In the processes disclosed herein, the conversion reaction can comprise conversion of furfural to 1,5-pentanediol. In the processes disclosed herein, the conversion of furfural to 1,5-pentanediol can comprise: contacting furfural with the hydrogen removed during the dehydrogenation reaction in the presence of a first catalyst at a first temperature and a first pressure to yield furfuryl alcohol; and contacting furfuryl alcohol with the hydrogen removed during the dehydrogenation reaction in the presence of a second catalyst at a second temperature and a second pressure to yield 1,5-pentanediol; wherein the first catalyst and the second catalyst, the first temperature and the second temperature, and the first pressure and the second pressure can be the same or different; and wherein the dehydrogenation reaction and the conversion reaction can occur in one reaction vessel, or wherein the dehydrogenation reaction and the conversion reaction can occur in more than one reactor vessels, wherein the more than one reactor vessels can be functionally connected either continuously or discontinuously.

In the processes disclosed herein, the conversion reaction can comprise conversion of hydroxymethylfurfural to 1,6-hexanediol. In the processes disclosed herein, the conversion of hydroxymethylfurfural to 1,6-hexanediol can comprise: contacting hydroxymethylfurfural with the hydrogen removed during the dehydrogenation reaction in the presence of a first catalyst at a first temperature and a first pressure to yield bi-hydrodroxymethyl furan; contacting bi-hydrodroxymethyl furan with the hydrogen removed during the dehydrogenation reaction in the presence of a second catalyst at a second temperature and a second pressure to yield hexanetriol; contacting hexanetriol with the hydrogen removed during the dehydrogenation reaction in the presence of a third catalyst at a third temperature and a third pressure to yield 1,6-hexanediol; wherein the first catalyst, the second catalyst, and the third catalyst; the first temperature, the second temperature, and the third temperature; and the first pressure, the second pressure, and the third pressure can be the same or different; and wherein the dehydrogenation reaction and the conversion reaction can occur in one reaction vessel, or wherein the dehydrogenation reaction and the conversion reaction can occur in more than one reactor vessels, wherein the more than one reactor vessels are functionally connected either continuously or discontinuously.

In the processes disclosed herein, the conversion reaction can comprise conversion of 2,4-hydroxybutanoic acid to 1,4-butanediol. In the processes disclosed herein, the conversion of 2,4-hydroxybutanoic acid to 1,4-butanediol can comprise: contacting 2,4-hydroxybutanoic acid with the hydrogen removed during the dehydrogenation reaction in the presence of a first catalyst at a first temperature and a first pressure to yield 1,2,4-butanetriol; and contacting 1,2,4-butanetriol with the hydrogen removed during the dehydrogenation reaction in the presence of a second catalyst at a second temperature and a second pressure to yield 1,4-butanediol; wherein the first catalyst and the second catalyst, the first temperature and the second temperature, and the first pressure and the second pressure can be the same or different; and wherein the dehydrogenation reaction and the conversion reaction can occur in one reaction vessel, or wherein the dehydrogenation reaction and the conversion reaction can occur in more than one reactor vessels, wherein the more than one reactor vessels are functionally connected either continuously or discontinuously.

In the processes disclosed herein, a process can convert a biomass-derived molecule to a conversion product, and the process can comprise performing any of the methods disclosed herein.

Provided herein are systems configured to perform a process to convert a biomass-derived molecule to a conversion product. The processes can comprise: using a conversion reaction to convert the biomass-derived molecule to the conversion product; wherein the conversion reaction can comprise hydrogenation, hydrogenolysis, or hydrodeoxygenation; and using a dehydrogenation reaction as a source of hydrogen for the conversion reaction. In the systems disclosed herein, the dehydrogenation reaction can comprise dehydrogenation of 2-butanol to 2-butanone. In the systems disclosed herein, at least 40%, 45%, 50%, 55%, 60%, 65%, 70%, 75%, 80%, 85%, 90%, or 95% of 2-butanol can be dehydrogenated. In the systems disclosed herein, the percent weight yield of MEK from dehydrogenated 2-butanol can be at least 65%, 70%, 75%, 80%, 85%, 90%, or 95%.

In the systems disclosed herein, the system can further comprise diluting 2-butanol with a solvent, wherein the solvent can be inert in the conversion reaction. In the systems disclosed herein, the solvent can comprise a $C_4$-$C_{18}$ hydrocarbon. In the systems disclosed herein, the $C_4$-$C_{18}$ hydrocarbon can be selected from hexane, cyclohexane, heptane, octane, decane, or dodecane, or a combination thereof. In the systems disclosed herein, the system can further comprising catalyzing the dehydrogenation reaction and the conversion reaction with a catalyst. In the systems disclosed herein, catalyzing can be achieved using a copper-based catalyst, a Raney nickel-based catalyst, a metal containing organosilica-based catalyst, or an iridium complex-based catalyst, or a combination thereof. In the systems disclosed herein, catalyzing can be achieved using a co-catalyst, an enhancer, or a promoter, or a combination thereof. In the systems disclosed herein, the dehydrogenation reaction and the conversion reaction can occur in one reaction vessel; or the dehydrogenation reaction and the conversion reaction can occur in more than one reactor vessels, wherein the more than one reactor vessels are functionally connected either continuously or discontinuously.

In the systems disclosed herein, the conversion reaction can be performed under an inert gas. In the systems disclosed herein, the inert gas can be nitrogen. In the systems disclosed herein, the conversion reaction can be performed under pressure. In the systems disclosed herein, the conversion reaction can be performed under a pressure of 50, 100, 200, 300, 400, 500, 600, 700, 800, 900, 1000, 1100, or 1200 psi. In the systems disclosed herein, the conversion reaction can be performed at a temperature of 50, 60, 70, 80, 90, 100, 110, 120, 130, 140, 150, 160, 170, 180, 190, 200, 210, 220, 230, 240, 250, 260, 270, 280, 290, or 300° C. In the systems disclosed herein, the conversion reaction can be performed for a time period of 0.1, 0.5, 1, 2, 3, 4, 5, 6, 7, 8, 9, 10, 11, 12, 13, 14, 15, 16, 17, 18, 19, 20, 21, 22, 23, or 24 hours. In the systems disclosed herein, the biomass-derived molecule can be derived from lignocellulosic biomass.

In the systems disclosed herein, the conversion reaction can comprise conversion of furfural to 1,5-pentanediol. In the systems disclosed herein, the conversion of furfural to 1,5-pentanediol can comprise: contacting furfural with the hydrogen removed during the dehydrogenation reaction in the presence of a first catalyst at a first temperature and a first pressure to yield furfuryl alcohol; and contacting furfuryl alcohol with the hydrogen removed during the dehydrogenation reaction in the presence of a second catalyst at a second temperature and a second pressure to yield 1,5-pentanediol; wherein the first catalyst and the second catalyst, the first temperature and the second temperature, and the first pressure and the second pressure are the same or different; and wherein the dehydrogenation reaction and the conversion reaction occur in one reaction vessel, or wherein the dehydrogenation reaction and the conversion reaction occur in more than one reactor vessels, wherein the more than one reactor vessels are functionally connected either continuously or discontinuously.

In the systems disclosed herein, the conversion reaction can comprise conversion of hydroxymethylfurfural to 1,6-hexanediol. In the systems disclosed herein, the conversion of hydroxymethylfurfural to 1,6-hexanediol can comprise: contacting hydroxymethylfurfural with the hydrogen removed during the dehydrogenation reaction in the presence of a first catalyst at a first temperature and a first pressure to yield bi-hydrodroxymethyl furan; contacting bi-hydrodroxymethyl furan with the hydrogen removed during the dehydrogenation reaction in the presence of a second catalyst at a second temperature and a second pressure to yield hexanetriol; contacting hexanetriol with the hydrogen removed during the dehydrogenation reaction in the presence of a third catalyst at a third temperature and a third pressure to yield 1,6-hexanediol; wherein the first catalyst, the second catalyst, and the third catalyst; the first temperature, the second temperature, and the third temperature; and the first pressure, the second pressure, and the third pressure are the same or different; and wherein the dehydrogenation reaction and the conversion reaction occur in one reaction vessel, or wherein the dehydrogenation reaction and the conversion reaction occur in more than one reactor vessels, wherein the more than one reactor vessels are functionally connected either continuously or discontinuously.

In the systems disclosed herein, the conversion reaction can comprise conversion of 2,4-hydroxybutanoic acid to 1,4-butanediol. In the systems disclosed herein, the conversion of 2,4-hydroxybutanoic acid to 1,4-butanediol can comprise: contacting 2,4-hydroxybutanoic acid with the hydrogen removed during the dehydrogenation reaction in the presence of a first catalyst at a first temperature and a first pressure to yield 1,2,4-butanetriol; and contacting 1,2,4-butanetriol with the hydrogen removed during the dehydrogenation reaction in the presence of a second catalyst at a second temperature and a second pressure to yield 1,4-butanediol; wherein the first catalyst and the second catalyst, the first temperature and the second temperature, and the first pressure and the second pressure are the same or different; and wherein the dehydrogenation reaction and the conversion reaction occur in one reaction vessel, or wherein the dehydrogenation reaction and the conversion reaction occur in more than one reactor vessels, wherein the more than one reactor vessels are functionally connected either continuously or discontinuously.

In the systems disclosed herein, the catalyst can comprise Pd, Pt, Rh, Ni, Ru, Cu/Si, Cu/zeolite, $Cu_2Cr_2O_5$, Ni/Cu/Si, $CuO/Al_2O_3$, Cu—Fe—Al, Cu—Zn—Al, Cu—Ni, Cu—MgO—$Cr_2O_3$, Au, lead-aluminum-borate, Raney nickel, Raney nickel/Cu, Raney nickel/Ag, Raney nickel/Au, Raney nickel/Sn, Raney nickel/Pb, Raney nickel/Zn, Raney nickel/Cd, Raney nickel/In, Raney nickel/Ge, MnO, NiO, MgO, Ir, CpIr, CpIr-N-heterocyclic carbene, organosilica, organotitania, organoallumina, organozirconia, Pd—Si—O—Si, Pt—Si—O—Si, Cu—Si—O—Si, Cu—Si—O—Si, $Cu_2Cr_2O_5$—Si—O—Si, RuSi—O—Si, Ir—Si—O—Si, Ag—Si—O—Si, Fe—Si—O—Si, Co—Si—O—Si, Rh—Si—O—Si, or a combination thereof. In the systems disclosed herein, catalyzing the dehydrogenation reaction and the conversion reaction can comprise using a second catalyst, wherein the second catalyst can comprise Pd, Pt, Rh, Ni, Ru, Cu/Si, Cu/zeolite, $Cu_2Cr_2O_5$, Ni/Cu/Si, CuO/$Al_2O_3$, Cu—Fe—Al, Cu—Zn—Al, Cu—Ni, Cu—MgO—$Cr_2O_3$, Au, lead-aluminum-borate, Raney nickel, Raney nickel/Cu, Raney nickel/Ag, Raney nickel/Au, Raney nickel/Sn, Raney nickel/Pb, Raney nickel/Zn, Raney nickel/Cd, Raney nickel/In, Raney nickel/Ge, MnO, NiO, MgO, Ir, CpIr, CpIr-N-heterocyclic carbene, organosilica, organotitania, organoallumina, organozirconia, Pd—Si—O—Si, Pt—Si—O—Si, Cu—Si—O—Si, Cu—Si—O—Si, $Cu_2Cr_2O_5$—Si—O—Si, RuSi—O—Si, Ir—Si—O—Si, Ag—Si—O—Si, Fe—Si—O—Si, Co—Si—O—Si, Rh—Si—O—Si, or a combination thereof. In the systems disclosed herein, catalyzing the dehydrogenation reaction and the conversion reaction can further comprise using a promoter. In the systems disclosed herein, the promoter can comprise CaO. In the systems disclosed herein, the promoter can comprise BaO. In the systems disclosed herein, the promoter can comprise ZrO. In the systems disclosed herein, the promoter can comprise $K_2O$. In the systems disclosed herein, the promoter can comprise MgO. In the systems disclosed herein, the method can further comprise diluting 2-butanol with a solvent. In the systems disclosed herein, the solvent can comprise hexane. In the systems disclosed herein, the solvent can comprise cyclohexane. In the systems disclosed herein, the solvent can comprise heptane. In the systems disclosed herein, the solvent can comprise octane. In the systems disclosed herein, the solvent can comprise decane. In the systems disclosed herein, the solvent can comprise dodecane. In the systems disclosed herein, the solvent can comprise isoparaffinic fluids.

In the systems disclosed herein, a system can be configured to perform a process to convert a biomass-derived molecule to a conversion product, wherein the process can comprise any of the processes disclosed herein.

DETAILED DESCRIPTION OF THE INVENTION

Figure 1A:
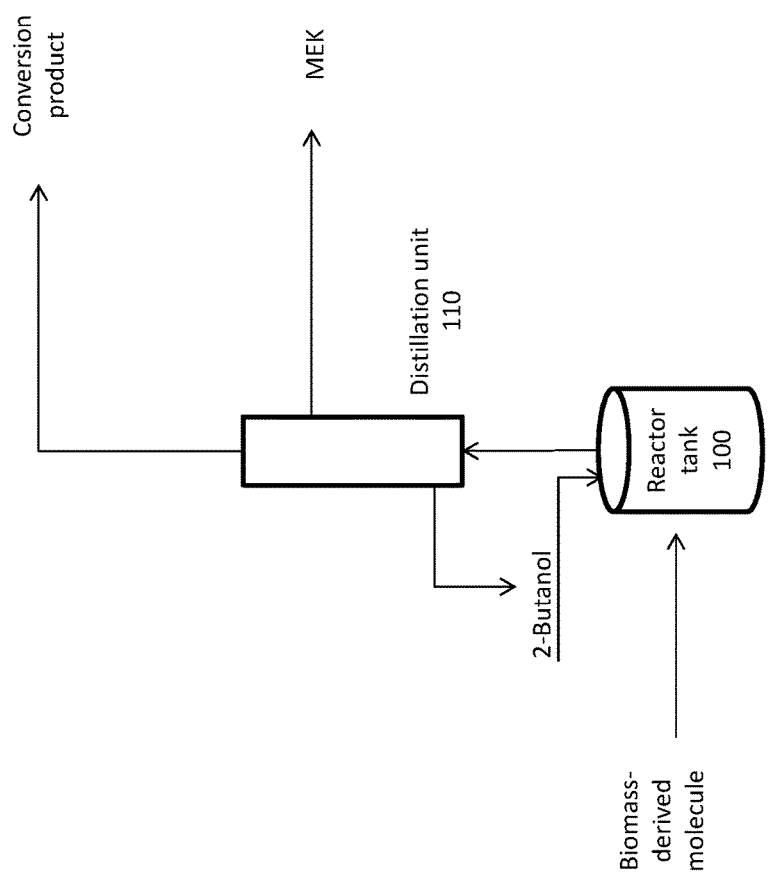
FIG. 1A shows a simplified flow scheme for the coupled dehydrogenation and conversion reactions.

The present disclosure relates to methods, processes, and systems for utilizing the dehydrogenation of 2-butanol as a hydrogen source for hydrogen-consuming hydrogenation, hydrogenolysis, or hydrodeoxygenation reactions of biomass or biomass-derived molecules.

The present methods, processes, and systems can be applied universally to any number of hydrogen accepting reactions known to those of skill in the art. One of ordinary skill in the art could readily identify suitable hydrogen accepting reactions for pairing with the dehydrogenation of 2-butanol to 2-butanone. In these reactions, the hydrogen produced by the dehydrogenation reaction acts as the hydrogen donor in the conversion reaction to which it is coupled.

Biomass is an alternative source for important chemicals currently made from petroleum derivatives, including, but not limited to, various organic acids, alcohols, polyols, as well as solvents such as benzene, toluene, xylene, and tetrahydrofuran (THF). Technologies to refine crude biomass to pure products of lignin and hemicellulose and cellulosic sugars are currently being developed. The products of these processes are sugars and lignin, which can require additional chemical processing to chemically convert them to a wide array of useful chemicals that can be used as substitutes for petrochemicals.

Notable steps of the chemical conversion of lignocellulosic-derived molecules involve the hydrogenation, hydrogenolysis, or hydrodeoxygenation of one or more chemical moieties of the molecule. Typically, these reactions are performed using isolated molecular hydrogen under high pressure of hydrogen gas, typically over 60 bar pressure of hydrogen (870 Psi).

The methods, processes, and systems of the present disclosure are conducted under conditions that effect hydrogenation, hydrogenolysis, or hydrodeoxygenation. Specifically, the hydrogenation or catalytic transfer hydrogenation of biomass or biomass-derived molecules. The catalytic transfer hydrogenation of biomass or biomass-derived molecules is initiated by the release of hydrogen from the hydrogen-donor material, 2-butanol. The conversion reactions are driven by the in situ hydrogen generation from the dehydrogenation of 2-butanol. 2-butanol is dehydrogenated to MEK according to the reaction:

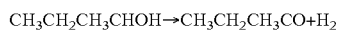

$$CH_3CH_2CH_3CHOH \rightarrow CH_3CH_2CH_3CO + H_2$$

Any biomass or biomass-derived molecule that can undergo hydrogenation, hydrogenolysis, or hydrodeoxygenation can be converted according to the systems, methods, and processes herein. Biomass can include, but is not limited to, any lignocellulosic material. Lignocellulosic material can include, but is not limited to, materials comprising hemicellulose, cellulose, lignin, lignin derivatives, starch, oligosaccharides, monosaccharides, dehydrated saccharides, halodehydrated saccharides, dehydrated and partially hydrogenated saccharides, or hydrogenated saccharides. Lignocellulosic material can also include composite materials that contain not only lignocellulosic polymers, but also a wide variety of small amounts of lipophilic or amphiphilic compounds, e.g., fatty acids, rosin acids, phytosteroids, as well as proteins and ash elements. Preferably, lignocellulosic material can be derived from non-food sources. Lignocellulosic materials are renewable sources for the production of amino acids for feed and food supplements, monomers and polymers for the plastic industry, and renewable sources for different types of fuels, polyol sugar substitutes (xylitol, sorbitol, manitols and the like), and numerous other chemicals that can be synthesized from $C_5$ and $C_6$ sugars.

A biomass or biomass-derived molecule that is converted through the coupling of the dehydration of 2-butanol (2-BuOH) to MEK to the conversion reaction can be derived from refined hemicellulose or cellulose sugars. Refined hemicellulose or cellulose sugars can be derived from lignocellulosic material by processing and refining processes, which generally comprises pretreatment, hemicellulose sugar extraction and purification, cellulose hydrolysis and cellulose sugar refining, lignin processing and refining, and direct lignin extraction. Biomass-derived molecules derived from refining of hemicellulose and cellulose sugars include, but are not limited to furfural, halofurfural, methyl furfural, furfuryl alcohol, methyl furfuryl alcohol, (methoxymethyl)-methyl furfural, hydroxymethylfurfural, 2-methylfuran, dimethylfuran, 2,5-bis(hydroxymethyl)furan, 5-hydroxymethyl-2-[(1-methylethoxy)methyl] furan, and 2-methyl-5[(1-methylmethoxy)methyl] furan, bis(1-methoxyethyxy)-methyl furan, tetrahydrofuran, levoglucosenone, 1,2,6-hexanetriol, 1,2,5-pentanetriol, 1,2,4-butanetriol, 2,4-dihydroxy butanoic acid, succinic acid, malic acid, or maleic acid.

As used herein, the terms percent weight yield, percent conversion, percent mole yield, theoretical yield, and percent selectivity are defined according to Equations (I)-(V) below:

$$\% \text{ Weight Yield} = \frac{\text{Wt of product}}{\text{Wt of reactant}} \times 100 \quad (I)$$

$$\% \text{ Conversion} = \left(1 - \frac{\text{Wt of reactant, g}}{\text{Wt of reactant at } t_0, \text{g}}\right) \times 100 \quad (II)$$

$$\% \text{ Mole yield} = \frac{\text{Wt of product, g}}{\text{Theoretical wt of product, g}} \times 100 \quad (III)$$

$$\text{Theoretical yield} = \frac{\text{Wt of reactant, g}}{\text{Reactant MW, g/mol}} \times \text{Product MW, g/mol} \quad (IV)$$

$$\% \text{ Selectivity} = \frac{\% \text{ Mole yield}}{\% \text{ Conversion}} \times 100 \quad (V)$$

The abbreviation "MEK" refers to methyl ethyl ketone. The terms "MEK," "methyl ethyl ketone," and "2-butanone" are used interchangeably.

As used herein, where the indefinite article "a" or "an" is used with respect to a statement or description of the presence of a step in a process disclosed herein, unless the statement or description explicitly provides to the contrary, the use of such indefinite article does not limit the presence of the step in the process to one in number. As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed.

Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains," or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or.

As used herein, the term "about" refers to variation in the reported numerical quantity that can occur. The term "about" means within 10, 9, 8, 7, 6, 5, 4, 3, 2, or 1% of the reported numerical value.

Systems for Producing MEK and a Conversion Product

The present systems can be applied universally to any number of hydrogen accepting reactions known to those of skill in the art. One of ordinary skill in the art could readily identify suitable hydrogen accepting reactions for pairing with the dehydrogenation of 2-butanol to 2-butanone. In these reactions, the hydrogen produced by the dehydrogenation reaction acts as the hydrogen donor in the conversion reaction to which it is coupled.

Provided herein are systems to convert a biomass or biomass-derived molecule to form a conversion product through the coupling of the dehydration of 2-butanol to MEK to the conversion reaction. Specifically, the hydrogen produced by the dehydrogenation of 2-butanol to MEK acts as the hydrogen donor in the conversion reaction.

Figure 1B:
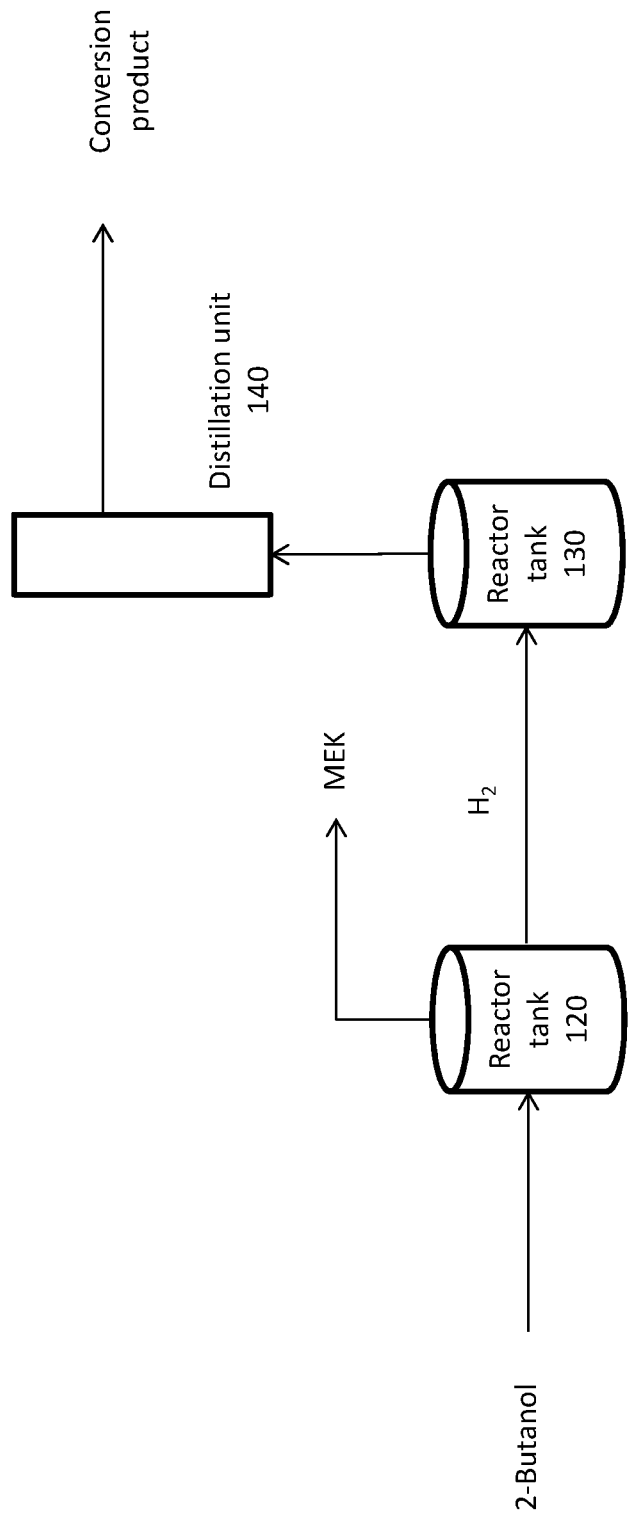
FIG. 1B shows an alternative simplified flow scheme for the coupled dehydrogenation and conversion reactions.

A schematic diagram of an exemplary system for producing MEK and a conversion product is shown in FIG. 1A and FIG. 1B. In general, the systems of FIG. 1A and FIG. 1B convert a biomass or biomass-derived molecule to form a conversion product through the coupling of the dehydration of 2-butanol (2-BuOH) to MEK to the conversion reaction. Specifically, the hydrogen produced by the dehydrogenation of 2-butanol to MEK acts as the hydrogen donor in the conversion reaction. In addition to hydrogen and MEK, the dehydrogenation reaction of 2-butanol can produce, in smaller quantities, additional by-products. Such by-products can include ethers formed by the condensation of 2-butanol with the alcohol groups present on the reactants or reaction intermediates. For example, at least one of di-sec-butyl ether, 5-[(1-methylpropoxy)methyl]-2-Furancarboxaldehyde, 5-hydroxymethyl-2-[(1-methylpropoxy)methyl]furan, 2-methyl-5-[(1-methylpropoxy)methyl]furan, or 2,5-[bis(1-methylpropoxy)-methyl]furan can be formed as a by-product of the dehydrogenation reaction. These ethers can be hydrolyzed under appropriate reaction conditions to release 2-butanol and the other alcohols, which are then converted to MEK and the target product.

In FIG. 1A, the dehydrogenation reaction and the conversion reaction occur in the same reactor tank 100. The system has an input that incorporates a biomass or biomass-derived molecule into the system. A biomass or biomass-derived molecule is added to reactor tank 100 either mechanically or via an input valve. The input of the biomass or biomass-derived molecule can be batch wise or constant flow. The system also has an input that incorporates 2-butanol into the system. 2-butanol is added to reactor tank 100 either mechanically or via an input valve. The input of 2-butanol can be batch wise or constant flow. A catalyst can be introduced into reactor tank 100. The catalyst can comprise Pd, Pt, Rh, Ni, Ru, Cu/Si, Cu/zeolite, $Cu_2Cr_2O_5$, Ni/Cu/Si, $CuO/Al_2O_3$, Cu—Fe—Al, Cu—Zn—Al, Cu—Ni, Cu—MgO—$Cr_2O_3$, Au, lead-aluminum-borate, Raney nickel, Raney nickel/Cu, Raney nickel/Ag, Raney nickel/Au, Raney nickel/Sn, Raney nickel/Pb, Raney nickel/Zn, Raney nickel/Cd, Raney nickel/In, Raney nickel/Ge, MnO, NiO, MgO, Ir, CpIr, CpIr-N-heterocyclic carbene, organosilica, organotitania, organoallumina, organozirconia, Pd—Si—O—Si, Pt—Si—O—Si, Cu—Si—O—Si, Cu—Si—O—Si, $Cu_2Cr_2O_5$—Si—O—Si, RuSi—O—Si, Ir—Si—O—Si, Ag—Si—O—Si, Fe—Si—O—Si, Co—Si—O—Si, Rh—Si—O—Si, or a combination thereof. A co-catalyst can also be introduced into reactor tank 100. A promoter can also be introduced into reactor tank 100. A solvent can also be introduced into reactor tank 100. The contents of reactor tank 100 are allowed to react for a sufficient amount of time and at appropriate reaction conditions to yield the desired products. Upon sufficient dehydrogenation and conversion, the contents of reactor 100 are directed to distillation unit 110, where product separation occurs. Unreacted 2-butanol can be returned to reactor tank 100 for further reaction, while MEK and a conversion product are collected at the head. The percent weight yield of MEK from 2-butanol can be at least about 65%, 70%, 75%, 80%, 85%, 90%, or 95% (wt/wt), or the percent weight yield of MEK from dehydrogenated 2-butanol can be at least about 65%, 70%, 75%, 80%, 85%, 90%, or 95%. The conversion product stream can comprise at least about 50 ppb, 60 ppb, 70 ppb, 80 ppb, 90 ppb, 100 ppb, 110 ppb, 120 ppb, 130 ppb, 140 ppb, or 150 ppb of a marker molecule. The marker molecule can comprise 2-butanol, 2-butanone, 5-[(1-methylpropoxy)methyl]-2-furancarboxaldehyde, 5-hydroxymethyl-2-[(1-methylpropoxy)methyl]furan, 2-methyl-5-[(1-methylpropoxy)methyl]furan, or 2,5-[bis(1-methylpropoxy)-methyl]furan, or a combination thereof.

Alternatively, the dehydrogenation reaction and the conversion reaction occur in separate reactor tanks. For example, in FIG. 1B, the dehydrogenation reaction occurs in reactor tank 120 and the conversion reaction occurs in reactor tank 130. The system has an input that incorporates 2-butanol into the system. 2-butanol is added to reactor tank 120 either mechanically or via an input valve. The input of 2-butanol can be batch wise or constant flow. A catalyst can be introduced into reactor tank 120. The catalyst can comprise Pd, Pt, Rh, Ni, Ru, Cu/Si, Cu/zeolite, $Cu_2Cr_2O_5$, Ni/Cu/Si, $CuO/Al_2O_3$, Cu—Fe—Al, Cu—Zn—Al, Cu—Ni, Cu—MgO—$Cr_2O_3$, Au, lead-aluminum-borate, Raney nickel, Raney nickel/Cu, Raney nickel/Ag, Raney nickel/Au, Raney nickel/Sn, Raney nickel/Pb, Raney nickel/Zn, Raney nickel/Cd, Raney nickel/In, Raney nickel/Ge, MnO, NiO, MgO, Ir, CpIr, CpIr-N-heterocyclic carbene, organosilica, organotitania, organoallumina, organozirconia, Pd—Si—O—Si, Pt—Si—O—Si, Cu—Si—O—Si, Cu—Si—O—Si, $Cu_2Cr_2O_5$—Si—O—Si, RuSi—O—Si, Ir—Si—O—Si, Ag—Si—O—Si, Fe—Si—O—Si, Co—Si—O—Si, Rh—Si—O—Si, or a combination thereof. A co-catalyst can also be introduced into reactor tank 120. A promoter can also be introduced into reactor tank 120. A solvent can also be introduced into reactor tank 120. The contents of reactor tank 120 allowed to react for a sufficient amount of time and at appropriate reaction conditions to yield the desired products. Upon sufficient dehydrogenation, the products can be separated. Unreacted 2-butanol can be separated, collected, and returned to reactor tank 120 for further reaction. The products of reactor tank 120 comprise MEK and hydrogen. The percent weight yield of MEK from 2-butanol can be at least about 65%, 70%, 75%, 80%, 85%, 90%, or 95% (wt/wt), or the percent weight yield of MEK from dehydrogenated 2-butanol can be at least about 65%, 70%, 75%, 80%, 85%, 90%, or 95%. Hydrogen produced by the dehydrogenation of 2-butanol is diverted to reactor tank 130. Reactor tank 120 and reactor tank 130 are functionally connected either directly or indirectly such that hydrogen produced by the dehydrogenation of 2-butanol can be introduced to tank 130. The introduction of hydrogen can be controlled such that the rate of release of molecular hydrogen into reactor tank 130 increases the yield of the conversion reaction to a desired product. For example, where mono-reduction is preferred over poly-reduction of a biomass-derived molecule.

Figure 2A:
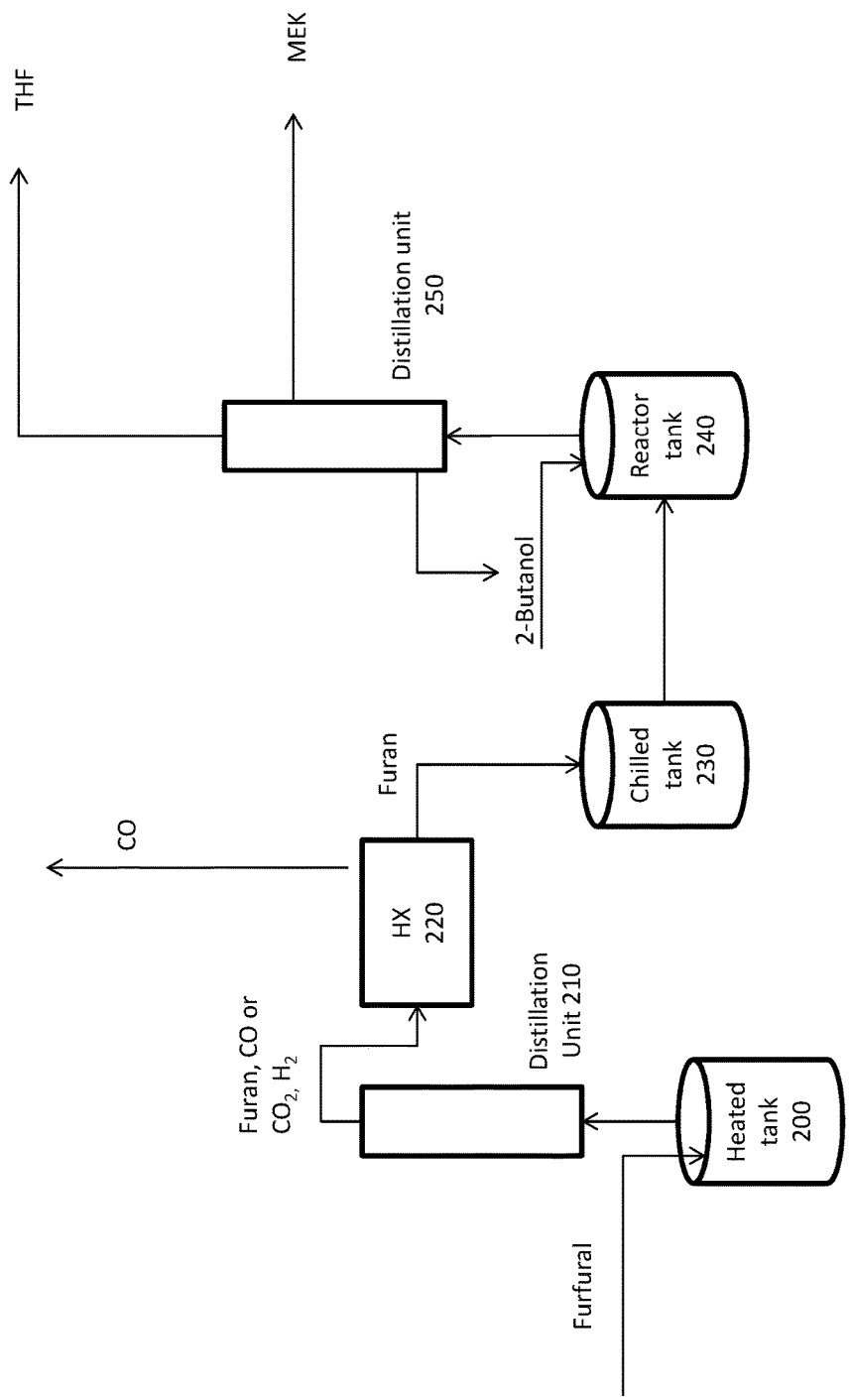
FIG. 2A shows a simplified flow scheme for the conversion of furfural to tetrahydrofuran (THF).
Figure 2B:
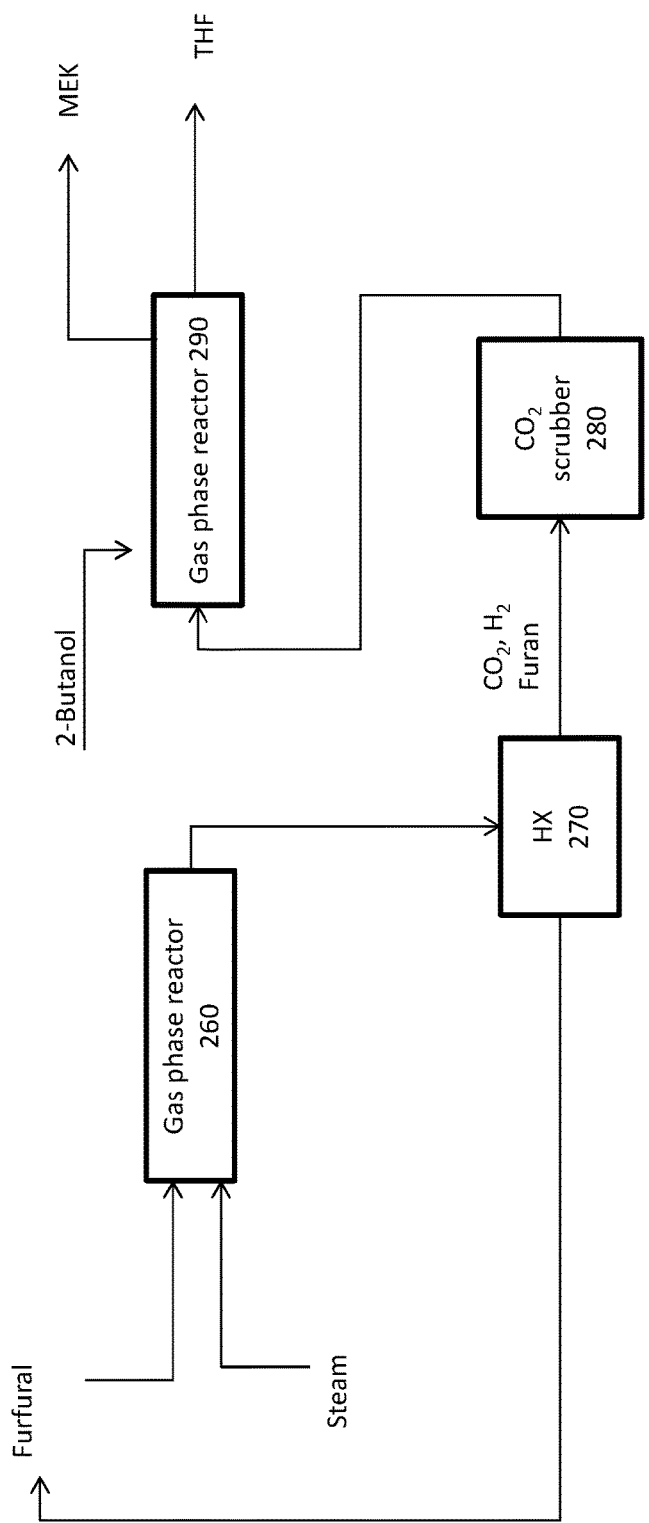
FIG. 2B shows an alternative simplified flow scheme for the conversion of furfural to THF.

Further, the system of FIG. 2B has an input that incorporates a biomass or biomass-derived molecule into the system. A biomass or biomass-derived molecule is added to reactor tank 130 either mechanically or via an input valve. The input of a biomass or biomass-derived molecule can be batch wise or constant flow. A catalyst can be introduced into reactor tank 130. A catalyst can comprise Pd, Pt, Rh, Ni, Ru, Cu/Si, Cu/zeolite, $Cu_2Cr_2O_5$, Ni/Cu/Si, $CuO/Al_2O_3$, Cu—Fe—Al, Cu—Zn—Al, Cu—Ni, Cu—MgO—$Cr_2O_3$, Au, lead-aluminum-borate, Raney nickel, Raney nickel/Cu, Raney nickel/Ag, Raney nickel/Au, Raney nickel/Sn, Raney nickel/Pb, Raney nickel/Zn, Raney nickel/Cd, Raney nickel/In, Raney nickel/Ge, MnO, NiO, MgO, Ir, CpIr, CpIr-N-heterocyclic carbene, organosilica, organotitania, organoalumina, organozirconia, Pd—Si—O—Si, Pt—Si—O—Si, Cu—Si—O—Si, Cu—Si—O—Si, $Cu_2Cr_2O_5$—Si—O—Si, RuSi—O—Si, Ir—Si—O—Si, Ag—Si—O—Si, Fe—Si—O—Si, Co—Si—O—Si, Rh—Si—O—Si, or a combination thereof. A co-catalyst can also be introduced into reactor tank 130. A promoter can also be introduced into reactor tank 130. A solvent can also be introduced into reactor tank 130. The contents of reactor tank 130 are allowed to react for a sufficient amount of time and at appropriate reaction conditions to yield the desired products. Upon sufficient conversion, the contents of reactor 130 are directed to distillation unit 140, where product separation occurs. The conversion product stream can comprise at least about 50 ppb, 60 ppb, 70 ppb, 80 ppb, 90 ppb, 100 ppb, 110 ppb, 120 ppb, 130 ppb, 140 ppb, or 150 ppb of a marker molecule. The marker molecule can comprise 2-butanol, 2-butanone, 5-[(1-methylpropoxy)methyl]-2-furancarboxaldehyde, 5-hydroxymethyl-2-[(1-methylpropoxy)methyl]furan, 2-methyl-5-[(1-methylpropoxy)methyl]furan, or 2,5-[bis(1-methylpropoxy)-methyl]furan, or a combination thereof.

As is illustrated in FIG. 1A and FIG. 1B, the dehydrogenation reaction and the conversion reaction can be conducted in the same reactor tank, or can be performed in separate reactor tanks that are functionally connected such that hydrogen produced by the dehydration of 2-butanol is introduced to the reactor tank where the conversion reaction is carried out. Reaction conditions are selected so as to optimize the dehydrogenation of 2-butanol to MEK and the conversion of the biomass or biomass-derived molecule to the desired product, whether the dehydrogenation and conversion reactions occur in the same or separate tanks. Accordingly, the dehydrogenation of 2-butanol as disclosed herein can occur in the same or in a separate reaction tank or under the same or different reaction conditions of the conversion reaction unless otherwise specified. Likewise, the conversion of a biomass or biomass-derived molecule as disclosed herein can occur in either the same or in a separate reaction tank or under the same or different reaction conditions of the dehydrogenation reaction unless otherwise specified.

Reaction conditions of the systems exemplified by FIG. 1A, FIG. 1B, FIG. 2A, and FIG. 2B can be controlled using a reaction control unit operably connected to the system. The reaction control unit can include a computer configured to receive input regarding the reaction parameters. The reaction parameters can include, but are not limited to, reaction time, reaction temperature, reaction pressure, as well as the identity, quantity, and concentration of reactants and products. The reaction control unit can use the variables of, for example, reaction temperature, reaction pressure, and the identity, quantity, and concentration of reactants and products at a particular time in order to calculate appropriate changes to the reaction parameters and in order to effect control of the reaction parameters.

Reaction conditions can be selected and controlled so as to optimize the yield of MEK from the dehydrogenation of 2-butanol. Specifically, reaction conditions can be selected and controlled such that at least 40%, 45%, 50%, 55%, 60%, 65%, 70%, 75%, 80%, 85%, 90%, or 95% of 2-butanol is dehydrogenated. Reaction conditions can be selected and controlled such that at least 40%, 45%, 50%, 55%, 60%, 65%, 70%, 75%, 80%, 85%, 90%, or 95% of dehydrogenated 2-butanol yields 2-butanone. Reaction conditions can be selected and controlled such that the percent weight yield of MEK from 2-butanol is at least about 65%, 70%, 75%, 80%, 85%, 90%, or 95% (wt/wt), or the percent weight yield of MEK from dehydrogenated 2-butanol is at least about 65%, 70%, 75%, 80%, 85%, 90%, or 95%. Reaction conditions can be selected and controlled such that the coupled dehydrogenation and conversion reactions have selectivity to a desired product greater than 40%, 50%, 60%, 70%, 80%, or 90%, and weight yield greater than 40%, 50%, 60%, 70%, 80%, or 90%.

The reaction control unit can be configured to control the input of 2-butanol or a biomass or biomass-derived molecule such that the molar ratio of 2-butanol to a biomass or biomass-derived molecule is about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.0, 9.5, or 10.0. An inert gas can be used during one or more of the reactions of this disclosure. The inert gas can be added at room temperature. For example, the reaction control unit can be configured to introduce nitrogen at room temperature to pressure of about 50, 100, 200, 300, 400, 500, 600, 700, 800, 900, 1000, 1100, or 1200 psi. Preferably, the reaction is performed under a pressure of about 200 to about 1200 psi. The reaction control unit can be configured to control the reaction temperature so that it is less than about 300, 290, 280, 270, 260, 250, 240, 230, 220, 210, 200, 190, 180, 170, 160, 150, 140, 130, 120, 110, 100, 90, 80, 70, 60, 50, 40, 30, or 25° C. The reaction control unit can be configured to control the reaction temperature so that it is over about 50, 60, 70, 80, 90, 100, 110, 120, 130, 140, 150, 160, 170, 180, 190, 200, 210, 220, 230, 240, 250, 260, 270, 280, 290, or 300° C. The reaction control unit can also be configured to control the reaction temperature so that it is between about 70 to about 300° C. or between about 180 to about 220° C. The reaction control unit can be configured to control the reaction time so that the reaction is carried out for less than about 0.1, 0.5, 1, 2, 3, 4, 5, 6, 7, 8, 9, 10, 11, 12, 13, 14, 15, 16, 17, 18, 19, or 20 hours. The reaction control unit can be configured to control the reaction time so that the reaction is carried out for at least about 0.1, 0.5, 1, 2, 3, 4, 5, 6, 7, 8, 9, 10, 11, 12, 13, 14, 15, 16, 17, 18, 19, 20, 21, 22, 23, or 24 hours. The reaction control unit can also be configured to control the reaction time so that the reaction is carried out for between about 2 to about 20 hours or between about 4 to about 10 hours.

The system can have an input that incorporates a solvent into the system. 2-butanol can be the sole solvent, or it can be diluted with an additional solvent, where the additional solvent is inert in the reaction. The additional solvent can be a $C_4$-$C_{18}$ hydrocarbon. The range of $C_4$-$C_{18}$ includes individual components, such as $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, or any sub-combinations thereof, such as, but not limited to, $C_6$-$C_{12}$, $C_5$-$C_{17}$, $C_6$-$C_{16}$, $C_7$-$C_{15}$, $C_8$-$C_{14}$, or $C_9$-$C_{13}$. The solvent can contain 6, 7, 8, 9, 10, 11, or 12 carbons. For example, suitable solvents include, but are not limited to, hexane, cyclohexane, heptane, octane, decane, dodecane, or a mixture thereof. Suitable solvents can also be commercial solvent mixtures including, but not limited to, isoparaffinic fluids (available from ExxonMobil). The additional solvent can be selected according to its ability to dissolve the reactants or the products, its boiling point, its availability, or price, or any other chemical or industrial consideration.

A catalyst can be introduced into the system. Both the dehydrogenation and the conversion reaction can occur using a catalyst, whether the conversion reaction and the dehydrogenation reaction occur in the same or separate reactor tanks. Depending on the specific biomass or biomass-derived molecules to be converted and the desired product or products, the catalysts used to catalyze the dehydrogenation reaction can also be used to catalyze the conversion reaction. Alternatively, an additional catalyst can be used to catalyze the conversion reaction. Also, catalysis can be enhanced by introducing a co-catalyst, promoter, enhancer, or a combination thereof.

The catalyst that is introduced into the system can affect the efficiency of the coupling of the dehydrogenation reaction to the conversion reaction. The suitability of a catalyst will vary depending on the functional groups present on the biomass or biomass-derived molecule, and on the desired conversion product. Not all functional groups have the same reactivity towards conversion. Therefore, the functional groups present on the biomass or biomass-derived molecule can affect the choice of the catalyst substrate structure, metal, or ligands. The functional groups present on the biomass or biomass-derived molecule can also affect whether a co-catalyst, promoter, Brønsted or Lewis acid or base, or solvents are introduced into the system. A catalyst can be selected according to the structure of the biomass or biomass-derived molecule, or according to other factors, such as its activity and selectivity, as well as its ability to be regenerated. Certain exemplary catalysts, co-catalysts, and promotors for use with the dehydrogenation and conversion reactions are described below. Additional suitable catalysts, co-catalysts, and promoters can be known in the art.

A suitable catalyst can contain a transition metal. For example, the catalyst can comprise Pd, Pt, Rh, Ni, or Ru. A suitable catalyst can comprise copper, which can include, but is not limited to, supported copper, copper oxide, and copper chromite catalysts. A suitable copper based catalyst can comprise Cu/Si, Cu/zeolite, $Cu_2Cr_2O_5$, Ni/Cu/Si, CuO/$Al_2O_3$, Cu—Fe—Al alloy, Cu—Zn—Al alloy, or Cu—Ni. Additionally, a suitable copper-based catalyst can have the formula $xCu-yMgO-zCr_2O_3$, where x, y, and z are the amounts in terms of weight percent of Cu, MgO, and $Cr_2O_3$, respectively. Specifically, the copper based catalyst can have a Cu content of about 5 to about 50 weight percent, preferably of about 10 to about 25 weight percent; a $Cr_2O_3$ content of about 0 to about 15 weight percent, preferably of about 1 to about 10 weight percent; where the balance is MgO.

A suitable catalyst can comprise a bimetallic component. For example, Ru, Au or lead-aluminum-borate compounds can be used as catalysts. The catalyst can be Raney nickel or a Raney nickel mixture comprising Raney nickel and about 0.1% to about 10% (wt/wt) of Cu, Ag, Au, Sn, Pb, Zn, Cd, In, or Ge. A suitable catalyst can comprise Ru, Au, or a lead-aluminum-borate component, or the oxides of Mn, Ni, or Mg.

A suitable catalyst can comprise an Ir complex. The Ir complex can have one or more cyclopentadienyl ligands, N-heterocyclic carbene (NHC) ligands, or a combination thereof. Specifically, the catalyst can be a CpIr or a CpIr-N-heterocyclic carbene complex.

A suitable catalyst can comprise a nanomaterial-based component. Such a catalyst can comprise, for example, palladium nanoparticles. The nanomaterial can be dispersed in a medium, such as organosilica, organotitania, organoalumina, organozirconia, or a combination thereof.

A suitable catalyst can comprise a metal-containing organosilica component. The metal-containing organosilica component can comprise one or more metal catalysts or a metal catalyst precursor and silica, where the metal catalyst or a metal catalyst precursor is incorporated into a network of Si—O—Si bonds of silica. The metal-containing organosilica catalyst can be a transition metal or a metal of Group 3A, Group 4A, Group 5A, or Group 6A of the periodic table. The metal catalyst or metal catalyst precursor can comprise palladium, platinum, copper, copper oxide, copper chromite, ruthenium, iridium, silver, iron, cobalt, rhodium, or a combination thereof.

Any of the catalysts disclosed herein can be used with hexane. Any of the catalysts disclosed herein can be used with cyclohexane. Any of the catalysts disclosed herein can be used with heptane. Any of the catalysts disclosed herein can be used with octane. Any of the catalysts disclosed herein can be used with decane. Any of the catalysts disclosed herein can be used with dodecane. Any of the catalysts disclosed herein can be used with isoparaffinic fluids. Any of the catalysts disclosed herein can be used with a mixture comprising hexane, cyclohexane, heptane, octane, decane, dodecane, or isoparaffinic fluids.

The catalyzed reactions of the present disclosure can further comprise a promoter. The promoter can be incorporated into a reaction to, for example, prevent catalyst fouling. Exemplary promoters include, but are not limited to, CaO, BaO, ZrO, $K_2O$, MgO, or a combination thereof. Any of the catalysts disclosed herein can be used with CaO. Any of the catalysts disclosed herein can be used with Bao. Any of the catalysts disclosed herein can be used with ZrO. Any of the catalysts disclosed herein can be used with $K_2O$. Any of the catalysts disclosed herein can be used with MgO. Any of the catalysts disclosed herein can be used with a mixture comprising CaO, BaO, ZrO, $K_2O$, or MgO.

The systems disclosed herein can be used to perform any of the methods or process disclosed herein. The systems disclosed herein can be used to convert any biomass or biomass-derived molecule. For example, the system can be used to convert HMF to 1,6-hexanediol. The system can be used to convert 2,4-hydroxybutanoic acid to 1,4-butanediol. The system can be used to convert furfural to 1,5-pentanediol.

Methods for Producing MEK and a Conversion Product

The present methods can be applied universally to any number of hydrogen accepting reactions known to those of skill in the art. One of ordinary skill in the art could readily identify suitable hydrogen accepting reactions for pairing with the dehydrogenation of 2-butanol to 2-butanone. In these reactions, the hydrogen produced by the dehydrogenation reaction acts as the hydrogen donor in the conversion reaction to which it is coupled.

Provided herein are methods to convert a biomass or biomass-derived molecule to form a conversion product through the coupling of the dehydration of 2-butanol to MEK to the conversion reaction. Specifically, the hydrogen produced by the dehydrogenation of 2-butanol to MEK acts as the hydrogen donor in the conversion reaction.

Provided herein are methods for using 2-butanol as the hydrogen source for a conversion reaction. A method for using 2-butanol as the hydrogen source for a conversion reaction can comprise: dehydrogenating 2-butanol to yield 2-butanone; wherein hydrogen removed from the 2-butanol during dehydrogenating is the hydrogen source for the conversion reaction; and wherein the conversion reaction comprises hydrogenation, hydrogenolysis, or hydrodeoxygenation. Preferably, the methods disclosed herein do not comprise adding molecular hydrogen from an external source. Preferably, the methods disclosed herein do not comprise adding formic acid, isopropanol, or gaseous molecular hydrogen from a source other than the hydrogen removed from the 2-butanol during dehydrogenation.

The methods disclosed herein can comprise the conversion of a biomass or biomass-derived molecule to form a conversion product, where in a biomass or biomass-derived molecule is defined as disclosed above. The biomass or biomass-derived molecule can be derived from lignocellulosic biomass. The biomass or biomass-derived molecule can be selected from a saccharide, a dehydrated saccharide, a halodehydrated saccharide, a dehydrated and partially hydrogenated saccharide, or a hydrogenated saccharide, or a combination thereof. The saccharide or the dehydrated saccharide can be selected from monosaccharide, oligosaccharide, furfural, halofurfural, methyl furfural, furfuryl alcohol, methyl furfuryl alcohol, (methoxymethyl)-methyl furfural, hydroxymethylfurfural, 2-methylfuran, dimethylfuran, 2,5-bis(hydroxymethyl)furan, 5-hydroxymethyl-2-[(1-methylethoxy)methyl]furan, and 2-methyl-5[(1-methylmethoxy)methyl]furan, bis(1-methoxyethyxy)-methylfuran, tetrahydrofuran, or levoglucosenone, or a combination thereof. The dehydrated and partially hydrogenated saccharide can be selected from 1,2,6-hexanetriol, 1,2,5-pentanetriol, 1,2,4-butanetriol, 2,4-dihydroxy butanoic acid, or succinic acid, malic acid, maleic acid, or a combination thereof. The hydrogenated saccharide can be selected from xylitol, mannitol, sorbitol, erythritol, arabitol, or galactitol, or a combination thereof.

The dehydrogenation reaction and the conversion can reaction occur in one reaction tank, or the dehydrogenation reaction and the conversion reaction can occur in separate reaction tanks. Where the dehydrogenation reaction and the conversion reaction occur in separate reaction tanks, the reactor tanks are functionally connected either continuously or discontinuously.

Conditions of the dehydrogenation reaction and conditions of the conversion reaction can be selected in order to optimize the yield of the products of the reaction. The weight yield of the product of the methods herein can be at least about 40%, 45%, 50%, 55%, 60%, 65%, 70%, 75%, 80%, 85%, or 90%. And the selectivity to the product of the methods herein can be at least about 40%, 45%, 50%, 55%, 60%, 65%, 70%, 75%, 80%, 85%, or 90%. At least about 40%, 45%, 50%, 55%, 60%, 65%, 70%, 75%, 80%, 85%, 90%, or 95% of 2-butanol can be dehydrogenated. The percent weight yield of MEK from dehydrogenated 2-butanol can be at least about 65%, 70%, 75%, 80%, 85%, 90%, or 95%.

The molar ratio of 2-butanol to furfural can be about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.0, 9.5, or 10.0. Additionally, 2-butanol can be diluted with a solvent, and the solvent can be inert in the conversion reaction. The solvent can comprise a $C_4$-$C_{18}$ hydrocarbon. The range of $C_4$-$C_{18}$ includes individual components, such as $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, or any sub-combinations thereof, such as, but not limited to, $C_6$-$C_{12}$, $C_5$-$C_{17}$, $C_6$-$C_{16}$, $C_7$-$C_{15}$, $C_8$-$C_{14}$, or $C_9$-$C_{13}$. The solvent can contain 6, 7, 8, 9, 10, 11, or 12 carbons. For example, suitable solvents include, but are not limited to, hexane, cyclohexane, heptane, octane, decane, dodecane, or a mixture thereof. Suitable solvents can also be commercial solvent mixtures including, but not limited to, isoparaffinic fluids (available from ExxonMobil). The additional solvent can be selected according to its ability to dissolve the reactants or the products, its boiling point, its availability, or price, or any other chemical or industrial consideration.

The method can also comprise catalyzing the dehydrogenation reaction and the conversion reaction with a catalyst. The catalyzing can be achieved using a copper based catalyst, a Raney nickel based catalyst, a metal containing organosilica based catalyst, or an iridium complex based catalyst, or a combination thereof. The catalyzing can be achieved using a co-catalyst, an enhancer, or a promoter, or a combination thereof.

Both the dehydrogenation and the conversion reaction can occur a catalyst, whether the conversion reaction and the dehydrogenation reaction occur in the same or separate reactor tanks. Depending on the specific biomass or biomass-derived molecules to be converted and the desired product or products, the catalysts used to catalyze the dehydrogenation reaction can also be used to catalyze the conversion reaction. Alternatively, an additional catalyst can be used to catalyze the conversion reaction. Also, catalysis can be enhanced by introducing a co-catalyst, promoter, enhancer, or a combination thereof.

The catalyst that is introduced into the reaction can affect the efficiency of the coupling of the dehydrogenation reaction to the conversion reaction. The suitability of a catalyst will vary depending on the functional groups present on the biomass or biomass-derived molecule, and on the desired conversion product. Not all functional groups have the same reactivity towards conversion. Therefore, the functional groups present on the biomass or biomass-derived molecule can affect the choice of the catalyst substrate structure, metal, or ligands. The functional groups present on the biomass or biomass-derived molecule can also affect whether a co-catalyst, promoter, Brønsted or Lewis acid or base, or solvents are introduced into the reaction. A catalyst can be selected according to the structure of the biomass or biomass-derived molecule, or according to other factors, such as its activity and selectivity, as well as its ability to be regenerated. Certain exemplary catalysts, co-catalysts, and promotors for use with the dehydrogenation and conversion reactions are described below. Additional suitable catalysts, co-catalysts, and promoters can be known in the art.

A suitable catalyst can contain a transition metal. For example, the catalyst can comprise Pd, Pt, Rh, Ni, or Ru. A suitable catalyst can comprise copper, which can include, but is not limited to, supported copper, copper oxide, and copper chromite catalysts. A suitable copper based catalyst can comprise Cu/Si, Cu/zeolite, $Cu_2Cr_2O_5$, Ni/Cu/Si, CuO/$Al_2O_3$, Cu—Fe—Al alloy, Cu—Zn—Al alloy, or Cu—Ni. Additionally, a suitable copper-based catalyst can have the formula xCu-yMgO-z$Cr_2O_3$, where x, y, and z are the amounts in terms of weight percent of Cu, MgO, and $Cr_2O_3$, respectively. Specifically, the copper based catalyst can have a Cu content of about 5 to about 50 weight percent, preferably of about 10 to about 25 weight percent; a $Cr_2O_3$ content of about 0 to about 15 weight percent, preferably of about 1 to about 10 weight percent; where the balance is MgO.

A suitable catalyst can comprise a bimetallic component. For example, Ru, Au or lead-aluminum-borate compounds can be used as catalysts. The catalyst can be Raney nickel or a Raney nickel mixture comprising Raney nickel and about 0.1% to about 10% (wt/wt) of Cu, Ag, Au, Sn, Pb, Zn, Cd, In, or Ge. A suitable catalyst can comprise Ru, Au, or a lead-aluminum-borate component, or the oxides of Mn, Ni, or Mg.

A suitable catalyst can comprise an Ir complex. The Ir complex can have one or more cyclopentadienyl ligands, N-heterocyclic carbene (NHC) ligands, or a combination thereof. Specifically, the catalyst can be a CpIr or a CpIr-N-heterocyclic carbene complex.

A suitable catalyst can comprise a nanomaterial-based component. Such a catalyst can comprise, for example, palladium nanoparticles. The nanomaterial can be dispersed in a medium, such as organosilica, organotitania, organoalumina, organozirconia, or a combination thereof.

A suitable catalyst can comprise a metal-containing organosilica component. The metal-containing organosilica component can comprise one or more metal catalysts or a metal catalyst precursor and silica, where the metal catalyst or a metal catalyst precursor is incorporated into a network of Si—O—Si bonds of silica. The metal-containing organosilica catalyst can be a transition metal or a metal of Group 3A, Group 4A, Group 5A, or Group 6A of the periodic table. The metal catalyst or metal catalyst precursor can comprise palladium, platinum, copper, copper oxide, copper chromite, ruthenium, iridium, silver, iron, cobalt, rhodium, or a combination thereof.

The catalyzed reactions of the present disclosure can further comprise a promoter. The promoter can be incorporated into a reaction to, for example, prevent catalyst fouling. Exemplary promoters include, but are not limited to, CaO, BaO, ZrO, $K_2O$, MgO, or a combination thereof. Any of the catalysts disclosed herein can be used with CaO. Any of the catalysts disclosed herein can be used with Bao. Any of the catalysts disclosed herein can be used with ZrO. Any of the catalysts disclosed herein can be used with $K_2O$. Any of the catalysts disclosed herein can be used with MgO. Any of the catalysts disclosed herein can be used with a mixture comprising CaO, BaO, ZrO, $K_2O$, or MgO.

The systems disclosed herein can be used to perform any of the methods or process disclosed herein. The systems disclosed herein can be used to convert any biomass or biomass-derived molecule. For example, the system can be used to convert HMF to 1,6-hexanediol. The system can be used to convert 2,4-hydroxybutanoic acid to 1,4-butanediol. The system can be used to convert furfural to 1,5-pentanediol.

The conversion reaction of the methods herein can comprise the conversion of furfural to 1,5-pentanediol. The conversion of furfural to 1,5-pentanediol can comprise contacting furfural with the hydrogen removed from the 2-butanol during dehydrogenation using a first catalyst at a first temperature and a first pressure to yield furfuryl alcohol; and contacting furfuryl alcohol with the hydrogen removed from the 2-butanol during dehydrogenation using a second catalyst at a second temperature and a second pressure to yield 1,5-pentanediol; wherein the first catalyst and the second catalyst, the first temperature and the second temperature, and the first pressure and the second pressure can the same or different; and wherein the dehydrogenation reaction and the conversion reaction occur in one reaction tank, or wherein the dehydrogenation reaction and the conversion reaction occur in more than one reactor tanks, wherein the more than one reactor tanks are functionally connected either continuously or discontinuously. The first catalyst of the method for the conversion of furfural to 1,5-pentanediol can be $xCu-yMgO-zCr_2O_3$, where x, y, and z are the amounts in terms of weight percent of Cu, MgO, and $Cr_2O_3$, respectively. Specifically, the copper based catalyst can have a Cu content of about 5 to about 50 weight percent, preferably of about 10 to about 25 weight percent; a $Cr_2O_3$ content of about 0 to about 15 weight percent, preferably of about 1 to about 10 weight percent; where the balance is MgO. The conversion of furfural to 1,5-pentanediol can be achieved by also using a co-catalyst, an enhancer, or a promoter. The conversion reaction can be achieved by catalyzing the reaction using a catalyst, wherein the catalyst can comprise any of the catalysts disclosed herein, or any known in the art. The first temperature of the method can be less than about 100, 110, 120, 130, 140, 150, 160, 170, 180, 190, 200, 210, 220, 230, 250, or 250° C.

The conversion reaction of the methods herein can comprise the conversion of hydroxymethylfurfural to 1,6-hexanediol. The conversion of hydroxymethylfurfural to 1,6-hexanediol can comprise contacting hydroxymethylfurfural with the hydrogen removed from the 2-butanol during dehydrogenation using a first catalyst at a first temperature and a first pressure to yield bi-hydrodroxymethyl furan; contacting bi-hydrodroxymethyl furan with the hydrogen removed from the 2-butanol during dehydrogenation using a second catalyst at a second temperature and a second pressure to yield hexanetriol; contacting hexanetriol with the hydrogen removed from the 2-butanol during dehydrogenation using a third catalyst at a third temperature and a third pressure to yield 1,6-hexanediol; wherein the first catalyst, the second catalyst, and the third catalyst; the first temperature, the second temperature, and the third temperature; and the first pressure, the second pressure, and the third pressure can the same or different; and wherein the dehydrogenation reaction and the conversion reaction occur in one reaction tank, or wherein the dehydrogenation reaction and the conversion reaction occur in more than one reactor tanks, wherein the more than one reactor tanks are functionally connected either or discontinuously. The conversion reaction can be achieved by catalyzing the reaction using a catalyst, wherein the catalyst can comprise any of the catalysts disclosed herein, or any known in the art.

At least about 40%, 45%, 50%, 55%, 60%, 65%, 70%, 75%, 80%, 85%, or 90% of converted hydroxymethylfurfural can be converted to 1,6-hexanediol. The first catalyst of the method can comprise a metal-containing organosilica catalyst comprising one or more metal catalyst or a precursor thereof and silica, wherein the metal catalyst or a precursor thereof is incorporated into a network of Si—O—Si bonds of the silica. The catalyst can comprise one or more metal catalyst or a precursor thereof and comprises Cu, CuO, $Cu_2Cr_2O_5$, Pd, PdO, Pt, Rh, Ru, Co, Fe, or Ag, or a combination thereof. The conversion of hydroxymethylfurfural to 1,6-hexanediol can be achieved using a co-catalyst, an enhancer, or a promoter, or a combination thereof. The methods disclosed herein can comprise processing 1,6-hexanediol to produce a commercial product. The commercial product comprises a polymer, wherein the polymer is selected from polyester, polyurethane, polyamide, polycarbonate, polyacetate or epoxy resin, or a combination thereof.

The conversion reaction of the methods herein can comprise conversion of 2,4-hydroxybutanoic acid to 1,4-butanediol. The conversion of 2,4-hydroxybutanoic acid to 1,4-butanediol can comprise contacting 2,4-hydroxybutanoic acid with the hydrogen removed from the 2-butanol during dehydrogenation using a first catalyst at a first temperature and a first pressure to yield 1,2,4-butanetriol; and contacting 1,2,4-butanetriol with the hydrogen removed from the 2-butanol during dehydrogenation using a second catalyst at a second temperature and a second pressure to yield 1,4-butanediol; wherein the first catalyst and the second catalyst, the first temperature and the second temperature, and the first pressure and the second pressure can be the same or different; and wherein the dehydrogenation reaction and the conversion reaction occur in one reaction tank, or wherein the dehydrogenation reaction and the conversion reaction occur in more than one reactor tanks, wherein the more than one reactor tanks are functionally connected either continuously or discontinuously. The conversion of 2,4-hydroxybutanoic acid to 1,4-butanediol can be achieved using a co-catalyst, an enhancer, or a promoter, or a combination thereof. The conversion reaction can be achieved by catalyzing the reaction using a catalyst, wherein the catalyst can comprise any of the catalysts disclosed herein, or any known in the art.

Processes for Producing MEK and a Conversion Product

The present processes can be applied universally to any number of hydrogen accepting reactions known to those of skill in the art. One of ordinary skill in the art could readily identify suitable hydrogen accepting reactions for pairing with the dehydrogenation of 2-butanol to 2-butanone. In these reactions, the hydrogen produced by the dehydrogenation reaction acts as the hydrogen donor in the conversion reaction to which it is coupled.

Provided herein are processes to convert a biomass or biomass-derived molecule to form a conversion product through the coupling of the dehydration of 2-butanol to MEK to the conversion reaction. Specifically, the hydrogen produced by the dehydrogenation of 2-butanol to MEK acts as the hydrogen donor in the conversion reaction.

Provided herein are processes to convert a biomass or biomass-derived molecule to a conversion product. The process can comprise a conversion reaction to convert the biomass or biomass-derived molecule to the conversion product; wherein the conversion reaction comprises hydrogenation, hydrogenolysis, or hydrodeoxygenation; and using a dehydrogenation reaction as a source of hydrogen for the conversion reaction. Optionally, does not comprise the addition of molecular hydrogen from an external source. Optionally, the process does not comprise addition of formic acid, isopropanol, or gaseous molecular hydrogen from a source other than the hydrogen produced from the dehydrogenation reaction. The dehydrogenation reaction can comprise the dehydrogenation of 2-butanol to 2-butanone. At least about 40%, 45%, 50%, 55%, 60%, 65%, 70%, 75%, 80%, 85%, 90%, or 95% of 2-butanol can be dehydrogenated. The percent weight yield of MEK from dehydrogenated 2-butanol can be at least about 65%, 70%, 75%, 80%, 85%, 90%, or 95%. The biomass or biomass-derived molecule converted according to the processes herein can be derived from lignocellulosic biomass.

The processes described herein can further comprise diluting 2-butanol with a solvent, wherein the solvent is inert in the conversion reaction. The solvent can comprise a $C_4$-$C_{18}$ hydrocarbon. The $C_4$-$C_{18}$ hydrocarbon can be selected from hexane, cyclohexane, heptane, octane, decane, or dodecane, or a combination thereof. The solvent can comprise a $C_4$-$C_{18}$ hydrocarbon. The range of $C_4$-$C_{18}$ includes individual components, such as $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, or any sub-combinations thereof, such as, but not limited to, $C_6$-$C_{12}$, $C_5$-$C_{17}$, $C_6$-$C_{16}$, $C_7$-$C_{15}$, $C_8$-$C_{14}$, or $C_9$-$C_{13}$. The solvent can contain 6, 7, 8, 9, 10, 11, or 12 carbons. For example, suitable solvents include, but are not limited to, hexane, cyclohexane, heptane, octane, decane, dodecane, or a mixture thereof. Suitable solvents can also be commercial solvent mixtures including, but not limited to, isoparaffinic fluids (available from ExxonMobil). The additional solvent can be selected according to its ability to dissolve the reactants or the products, its boiling point, its availability, or price, or any other chemical or industrial consideration.

The dehydrogenation reaction and the conversion reaction can occur in one reaction tank, or the dehydrogenation reaction and the conversion reaction can occur in more than one reaction tanks. Where the dehydrogenation reaction and the conversion reaction occur in more than one reactor tanks, the reactor tanks are functionally connected either continuously or discontinuously.

The processes disclosed herein can further comprise catalyzing the dehydrogenation reaction and the conversion reaction with a catalyst. The conversion reaction can be achieved by catalyzing the reaction using a catalyst, wherein the catalyst can comprise any of the catalysts disclosed herein, or any known in the art. The catalyzing can be achieved using a copper based catalyst, a Raney nickel based catalyst, a metal containing organosilica based catalyst, or an iridium complex based catalyst, or a combination thereof. The catalyzing can be achieved using a co-catalyst, an enhancer, or a promoter, or a combination thereof.

The catalyst that is introduced into the system can affect the efficiency of the coupling of the dehydrogenation reaction to the conversion reaction. The suitability of a catalyst will vary depending on the functional groups present on the biomass or biomass-derived molecule, and on the desired conversion product. Not all functional groups have the same reactivity towards conversion. Therefore, the functional groups present on the biomass or biomass-derived molecule can affect the choice of the catalyst substrate structure, metal, or ligands. The functional groups present on the biomass or biomass-derived molecule can also affect whether a co-catalyst, promoter, Brønsted or Lewis acid or base, or solvents are introduced into the system. A catalyst can be selected according to the structure of the biomass or biomass-derived molecule, or according to other factors, such as its activity and selectivity, as well as its ability to be regenerated. Certain exemplary catalysts, co-catalysts, and promotors for use with the dehydrogenation and conversion reactions are described below. Additional suitable catalysts, co-catalysts, and promoters can be known in the art.

A suitable catalyst can contain a transition metal. For example, the catalyst can comprise Pd, Pt, Rh, Ni, or Ru. A suitable catalyst can comprise copper, which can include, but is not limited to, supported copper, copper oxide, and copper chromite catalysts. A suitable copper based catalyst can comprise Cu/Si, Cu/zeolite, $Cu_2Cr_2O_5$, Ni/Cu/Si, CuO/$Al_2O_3$, Cu—Fe—Al alloy, Cu—Zn—Al alloy, or Cu—Ni. Additionally, a suitable copper-based catalyst can have the formula xCu-yMgO-zCr$_2$O$_3$, where x, y, and z are the amounts in terms of weight percent of Cu, MgO, and $Cr_2O_3$, respectively. Specifically, the copper based catalyst can have a Cu content of about 5 to about 50 weight percent, preferably of about 10 to about 25 weight percent; a $Cr_2O_3$ content of about 0 to about 15 weight percent, preferably of about 1 to about 10 weight percent; where the balance is MgO.

A suitable catalyst can comprise a bimetallic component. For example, Ru, Au or lead-aluminum-borate compounds can be used as catalysts. The catalyst can be Raney nickel or a Raney nickel mixture comprising Raney nickel and about 0.1% to about 10% (wt/wt) of Cu, Ag, Au, Sn, Pb, Zn, Cd, In, or Ge. A suitable catalyst can comprise Ru, Au, or a lead-aluminum-borate component, or the oxides of Mn, Ni, or Mg.

A suitable catalyst can comprise an Ir complex. The Ir complex can have one or more cyclopentadienyl ligands, N-heterocyclic carbene (NHC) ligands, or a combination thereof. Specifically, the catalyst can be a CpIr or a CpIr-N-heterocyclic carbene complex.

A suitable catalyst can comprise a nanomaterial-based component. Such a catalyst can comprise, for example, palladium nanoparticles. The nanomaterial can be dispersed in a medium, such as organosilica, organotitania, organoalumina, organozirconia, or a combination thereof.

A suitable catalyst can comprise a metal-containing organosilica component. The metal-containing organosilica component can comprise one or more metal catalysts or a metal catalyst precursor and silica, where the metal catalyst or a metal catalyst precursor is incorporated into a network of Si—O—Si bonds of silica. The metal-containing organosilica catalyst can be a transition metal or a metal of Group 3A, Group 4A, Group 5A, or Group 6A of the periodic table. The metal catalyst or metal catalyst precursor can comprise palladium, platinum, copper, copper oxide, copper chromite, ruthenium, iridium, silver, iron, cobalt, rhodium, or a combination thereof.

The catalyzed reactions of the present disclosure can further comprise a promoter. The promoter can be incorporated into a reaction to, for example, prevent catalyst fouling. Exemplary promoters include, but are not limited to, CaO, BaO, ZrO, $K_2O$, MgO, or a combination thereof.

The conversion reaction can be performed under an inert gas. The inert gas can be nitrogen. The conversion reaction can be performed under pressure. The conversion reaction can be performed under a pressure of about 50, 100, 200, 300, 400, 500, 600, 700, 800, 900, 1000, 1100, or 1200 psi. The conversion reaction can be performed at a temperature of about 50, 60, 70, 80, 90, 100, 110, 120, 130, 140, 150, 160, 170, 180, 190, 200, 210, 220, 230, 240, 250, 260, 270, 280, 290, or 300° C. The conversion reaction can be performed for a time period of about 0.1, 0.5, 1, 2, 3, 4, 5, 6, 7, 8, 9, 10, 11, 12, 13, 14, 15, 16, 17, 18, 19, 20, 21, 22, 23, or 24 hours.

The product of the processes can comprise at least about 50 ppb, 60 ppb, 70 ppb, 80 ppb, 90 ppb, 100 ppb, 110 ppb, 120 ppb, 130 ppb, 140 ppb, or 150 ppb of a marker molecule, wherein the marker molecule can comprise 2-butanol, 2-butanone, 5-[(1-methylpropoxy)methyl]-2-furancarboxaldehyde, 5-hydroxymethyl-2-[(1-methylpropoxy)methyl] furan, 2-methyl-5-[(1-methylpropoxy)methyl]furan, or 2,5-[bis(1-methylpropoxy)-methyl]furan, or a combination thereof.

The processes can comprise the conversion of furfural to 1,5-pentanediol. The conversion of furfural to 1,5-pentanediol can comprise contacting furfural with the hydrogen removed during the dehydrogenation reaction using a first catalyst at a first temperature and a first pressure to yield furfuryl alcohol; and contacting furfuryl alcohol with the hydrogen removed during the dehydrogenation reaction using a second catalyst at a second temperature and a second pressure to yield 1,5-pentanediol; wherein the first catalyst and the second catalyst, the first temperature and the second temperature, and the first pressure and the second pressure can the same or different; and wherein the dehydrogenation reaction and the conversion reaction occur in one reaction tank, or wherein the dehydrogenation reaction and the conversion reaction occur in more than one reactor tanks, wherein the more than one reactor tanks are functionally connected either continuously or discontinuously.

The processes can comprise the conversion of hydroxymethylfurfural to 1,6-hexanediol. The conversion of hydroxymethylfurfural to 1,6-hexanediol can comprises contacting hydroxymethylfurfural with the hydrogen removed during the dehydrogenation reaction using a first catalyst at a first temperature and a first pressure to yield bi-hydrodroxymethyl furan; contacting bi-hydrodroxymethyl furan with the hydrogen removed during the dehydrogenation reaction using a second catalyst at a second temperature and a second pressure to yield hexanetriol; contacting hexanetriol with the hydrogen removed during the dehydrogenation reaction using a third catalyst at a third temperature and a third pressure to yield 1,6-hexanediol; wherein the first catalyst, the second catalyst, and the third catalyst; the first temperature, the second temperature, and the third temperature; and the first pressure, the second pressure, and the third pressure can the same or different; and wherein the dehydrogenation reaction and the conversion reaction occur in one reaction tank, or wherein the dehydrogenation reaction and the conversion reaction occur in more than one reactor tanks, wherein the more than one reactor tanks are functionally connected either continuously or discontinuously.

The processes can comprise the conversion of 2,4-hydroxybutanoic acid to 1,4-butanediol. The conversion of 2,4-hydroxybutanoic acid to 1,4-butanediol can comprise contacting 2,4-hydroxybutanoic acid with the hydrogen removed during the dehydrogenation reaction using a first catalyst at a first temperature and a first pressure to yield 1,2,4-butanetriol; and contacting 1,2,4-butanetriol with the hydrogen removed during the dehydrogenation reaction using a second catalyst at a second temperature and a second pressure to yield 1,4-butanediol; wherein the first catalyst and the second catalyst, the first temperature and the second temperature, and the first pressure and the second pressure can the same or different; and wherein the dehydrogenation reaction and the conversion reaction occur in one reaction tank, or wherein the dehydrogenation reaction and the conversion reaction occur in more than one reactor tanks, wherein the more than one reactor tanks are functionally connected either continuously or discontinuously.

The processes disclosed herein can be used to perform any of the methods disclosed herein.

Conversion Reactions Using Donor Hydrogen Produced from the Dehydrogenation of 2-Butanol The present methods, processes, and systems can be applied universally to any number of hydrogen accepting reactions known to those of skill in the art. One of ordinary skill in the art could readily identify suitable hydrogen accepting reactions for pairing with the dehydrogenation of 2-butanol to 2-butanone. In these reactions, the hydrogen produced by the dehydrogenation reaction acts as the hydrogen donor in the conversion reaction to which it is coupled.

As disclosed above, numerous biomass or biomass-derived molecules can undergo conversion reactions. Accordingly, numerous biomass or biomass-derived molecules can be converted according to the methods, processes, and systems disclosed herein. Such biomass or biomass-derived molecules can be known in the art. The following sections provide non-limiting examples of the conversion of biomass or biomass-derived molecules by the coupling of the dehydrogenation of 2-butanol to 2-butanone to the conversion reaction.

1. Conversion of Furfural

The dehydration of 2-butanol to MEK can be coupled to the conversion of furfural (furaldehyde) to various products. As discussed above, the reaction conditions can be selected and controlled such that at least 40%, 45%, 50%, 55%, 60%, 65%, 70%, 75%, 80%, 85%, 90%, or 95% of 2-butanol is dehydrogenated. Reaction conditions can be selected and controlled such that at least 40%, 45%, 50%, 55%, 60%, 65%, 70%, 75%, 80%, 85%, 90%, or 95% of dehydrogenated 2-butanol yields 2-butanone. Reaction conditions can be selected and controlled such that the percent weight yield of MEK from 2-butanol is at least about 65%, 70%, 75%, 80%, 85%, 90%, or 95% (wt/wt), or the percent weight yield of MEK from dehydrogenated 2-butanol is at least about 65%, 70%, 75%, 80%, 85%, 90%, or 95%. Reaction conditions can be selected and controlled such that the coupled dehydrogenation and conversion reactions have selectivity to a desired product greater than 40%, 50%, 60%, 70%, 80%, or 90%, and weight yield greater than 40%, 50%, 60%, 70%, 80%, or 90%. The overall conversion of 2-butanol can be less than 100%, 80%, 60%, or 50%, and the molar yield of the dehydrogenated 2-butanol to MEK can be greater than 80%, 85%, 90%, or 95%.

Furfural can be derived from hemicellulose sugars via an acid-catalyzed conversion or an ionic liquid catalytic conversion. Furfural can undergo multiple conversions to a wide spectrum of high-value chemicals, including, but not limited to, 2-methyl furan, furfuryl alcohol, 1,5-pentanediol, or tetrahydrofuran (THF).

Furfural can be decarbonylated to form furan. Furfural can also be converted under catalytic reduction to tetrahydrofuran (THF).

FIG. 2A illustrates the conversion of furfural to THF in the liquid phase. Furfural can be introduced into the heated reactor 200 where it is decarbonylated to furan. A catalyst can be introduced into the heated reactor 200. A catalyst can comprise Pd, Pt, Rh, Ni, Ru, Cu/Si, Cu/zeolite, $Cu_2Cr_2O_5$, Ni/Cu/Si, $CuO/Al_2O_3$, Cu—Fe—Al, Cu—Zn—Al, Cu—Ni, Cu—MgO—$Cr_2O_3$, Au, lead-aluminum-borate, Raney nickel, Raney nickel/Cu, Raney nickel/Ag, Raney nickel/Au, Raney nickel/Sn, Raney nickel/Pb, Raney nickel/Zn, Raney nickel/Cd, Raney nickel/In, Raney nickel/Ge, MnO, NiO, MgO, Ir, CpIr, CpIr-N-heterocyclic carbene, organosilica, organotitania, organoallumina, organozirconia, Pd—Si—O—Si, Pt—Si—O—Si, Cu—Si—O—Si, Cu—Si—O—Si, $Cu_2Cr_2O_5$—Si—O—Si, RuSi—O—Si, Ir—Si—O—Si, Ag—Si—O—Si, Fe—Si—O—Si, Co—Si—O—Si, Rh—Si—O—Si, or a combination thereof. The products of the reaction in the heated reactor 200 enter the distillation unit 210, where product separation occurs. The unreacted furfural is condensed and can be returned to the heated reactor for further reaction, while furan, CO or $CO_2$, and $H_2$ are collected at the head. The stream can be contacted with base to remove $CO_2$. The products can be cooled via heat exchanger 220 and chilled tank 230. Furan and 2-butanol are introduced into reactor tank 240. A catalyst can be introduced into reactor tank 240. Any catalyst disclosed herein can be used, or any catalyst known in the art can be used. A catalyst can comprise Pd, Pt, Rh, Ni, Ru, Cu/Si, Cu/zeolite, $Cu_2Cr_2O_5$, Ni/Cu/Si, $CuO/Al_2O_3$, Cu—Fe—Al, Cu—Zn—Al, Cu—Ni, Cu—MgO—$Cr_2O_3$, Au, lead-aluminum-borate, Raney nickel, Raney nickel/Cu, Raney nickel/Ag, Raney nickel/Au, Raney nickel/Sn, Raney nickel/Pb, Raney nickel/Zn, Raney nickel/Cd, Raney nickel/In, Raney nickel/Ge, MnO, NiO, MgO, Ir, CpIr, CpIr-N-heterocyclic carbene, organosilica, organotitania, organoallumina, organozirconia, Pd—Si—O—Si, Pt—Si—O—Si, Cu—Si—O—Si, Cu—Si—O—Si, $Cu_2Cr_2O_5$—Si—O—Si, RuSi—O—Si, Ir—Si—O—Si, Ag—Si—O—Si, Fe—Si—O—Si, Co—Si—O—Si, Rh—Si—O—Si, or a combination thereof. A co-catalyst can also be introduced into reactor tank 240. A promoter can also be introduced into reactor tank 240. The products produced by the coupled dehydrogenation reaction and conversion reaction comprise MEK and THF.

FIG. 2B illustrates the conversion of furfural to THF in the gas phase. The reaction conditions for the reactions performed in the gas phase are similar to the reaction conditions for the reactions performed in the liquid phase. Fufural can be introduced into the gas phase reactor 260 with steam where it is decarbonylated to furan. A catalyst can be introduced into reactor 260. Any catalyst disclosed herein can be used, or any catalyst known in the art can be used. A catalyst can comprise Pd, Pt, Rh, Ni, Ru, Cu/Si, Cu/zeolite, $Cu_2Cr_2O_5$, Ni/Cu/Si, $CuO/Al_2O_3$, Cu—Fe—Al, Cu—Zn—Al, Cu—Ni, Cu—MgO—$Cr_2O_3$, Au, lead-aluminum-borate, Raney nickel, Raney nickel/Cu, Raney nickel/Ag, Raney nickel/Au, Raney nickel/Sn, Raney nickel/Pb, Raney nickel/Zn, Raney nickel/Cd, Raney nickel/In, Raney nickel/Ge, MnO, NiO, MgO, Ir, CpIr, CpIr-N-heterocyclic carbene, organosilica, organotitania, organoallumina, organozirconia, Pd—Si—O—Si, Pt—Si—O—Si, Cu—Si—O—Si, Cu—Si—O—Si, $Cu_2Cr_2O_5$—Si—O—Si, RuSi—O—Si, Ir—Si—O—Si, Ag—Si—O—Si, Fe—Si—O—Si, Co—Si—O—Si, Rh—Si—O—Si, or a combination thereof. The products of the reaction in the gas phase reactor 260 can be cooled via heat exchanger 270. Furan, CO or $CO_2$, and $H_2$ are collected at the head. $CO_2$ can be removed by the $CO_2$ scrubber 280. Furan and 2-butanol are introduced into reactor tank 290 under the reaction conditions described herein. A catalyst can be introduced into reactor tank 290. A catalyst can comprise Pd, Pt, Rh, Ni, Ru, Cu/Si, Cu/zeolite, $Cu_2Cr_2O_5$, Ni/Cu/Si, $CuO/Al_2O_3$, Cu—Fe—Al, Cu—Zn—Al, Cu—Ni, Cu—MgO—$Cr_2O_3$, Au, lead-aluminum-borate, Raney nickel, Raney nickel/Cu, Raney nickel/Ag, Raney nickel/Au, Raney nickel/Sn, Raney nickel/Pb, Raney nickel/Zn, Raney nickel/Cd, Raney nickel/In, Raney nickel/Ge, MnO, NiO, MgO, Ir, CpIr, CpIr-N-heterocyclic carbene, organosilica, organotitania, organoallumina, organozirconia, Pd—Si—O—Si, Pt—Si—O—Si, Cu—Si—O—Si, Cu—Si—O—Si, $Cu_2Cr_2O_5$—Si—O—Si, RuSi—O—Si, Ir—Si—O—Si, Ag—Si—O—Si, Fe—Si—O—Si, Co—Si—O—Si, Rh—Si—O—Si, or a combination thereof. A co-catalyst can also be introduced into reactor tank 290. A promoter can also be introduced into reactor tank 290. The products produced by the coupled dehydrogenation reaction and conversion reaction comprise MEK and THF.

In the reactions illustrated by FIG. 2A and FIG. 2B, furfural can be decarbonylated to furan in the liquid phase or the gas phase with the use of a suitable catalyst. Any catalyst disclosed herein can be used, or any catalyst known in the art can be used. A catalyst can comprise Pd, Pt, Rh, Ni, Ru, Cu/Si, Cu/zeolite, $Cu_2Cr_2O_5$, Ni/Cu/Si, $CuO/Al_2O_3$, Cu—Fe—Al, Cu—Zn—Al, Cu—Ni, Cu—MgO—$Cr_2O_3$, Au, lead-aluminum-borate, Raney nickel, Raney nickel/Cu, Raney nickel/Ag, Raney nickel/Au, Raney nickel/Sn, Raney nickel/Pb, Raney nickel/Zn, Raney nickel/Cd, Raney nickel/In, Raney nickel/Ge, MnO, NiO, MgO, Ir, CpIr, CpIr-N-heterocyclic carbene, organosilica, organotitania, organoallumina, organozirconia, Pd—Si—O—Si, Pt—Si—O—Si, Cu—Si—O—Si, Cu—Si—O—Si, $Cu_2Cr_2O_5$—Si—O—Si, RuSi—O—Si, Ir—Si—O—Si, Ag—Si—O—Si, Fe—Si—O—Si, Co—Si—O—Si, Rh—Si—O—Si, or a combination thereof. Heterogeneous catalysts can be used in either phase. Catalysts known to catalyze the decarbonylation of furfural to furan include, but are not limited to, Mn chromites, Zinc molibdate, copper molibdate, oxides of Zn, Cr, Mn, Al and their mixed oxides, Ni alloy catalysts, Ni/C, Ni/Cr oxide, Raney Ni, Al—Zn—Fe catalysts, Pd, Pt, Rh, Ru or Mo supported over carbon, silica, alumina, or various zeolites. A basic salt can be added as enhancer that extends catalyst life. Suitable salts include, but are not limited to, $Na_2CO_3$, $K_2CO_3$, $Cs_2CO_3$, and other alkali carbonates.

Furfural can undergo catalytic reduction to form furfuryl alcohol, and through a consecutive conversion, to 1,5-pentanediol. The conversion reactions can be performed using any catalyst disclosed herein or any catalyst known in the art. The catalyst can comprise $xCu\text{-}yMgO\text{-}zCr_2O_3$, where x, y, and z are the amounts in terms of weight percent of Cu, MgO, and $Cr_2O_3$, respectively. Specifically, the copper-based catalyst can have a Cu content of about 5 to about 50 weight percent, or of about 10 to about 25 weight percent; a $Cr_2O_3$ content of about 0 to about 15 weight percent, or of about 1 to about 10 weight percent; where the balance is MgO. The reaction temperature can be less than 200° C. in order to prevent undesired reactions, and thereby improve reaction selectivity.

Furfural can be reduced via catalytic reduction to form 2-methyl furan. Any catalyst disclosed herein can be used, or any catalyst known in the art can be used. The catalyst used to catalyze the reaction can contain a palladium component. For example, palladium on activated carbon or palladium on allumina can be used. Other palladium catalysts that can be used in this conversion reaction include, but are not limited to, $PdCl_2$ and $Pd_2(dba)_3$. The catalyst for this conversion reaction can also comprise Pt, Ru, Cu, Rh, or a combination thereof. Preferably, Ru/C can be used as the catalyst. The reaction temperature can be between about 70 to about 250° C. or between about 100 to about 200° C. The reaction can be carried out for a time between about 2 to about 20 hours or between about 4 to about 10 hours.

The resulting furan is hydrogenated either in liquid phase or in the gas phase using a hydrogenation catalysts. The source of hydrogen can be the $H_2$ released during the dehydrogenation of 2-butanol, or, additionally, from the $H_2$ released in the first stage.

2. Conversion of 5-(hydroxymethyl)furfural

The dehydration of 2-butanol to MEK can be coupled to the conversion of 5-(hydroxymethyl)furfural (HMF) to various products. As discussed above, the reaction conditions can be selected and controlled such that at least 40%, 45%, 50%, 55%, 60%, 65%, 70%, 75%, 80%, 85%, 90%, or 95% of 2-butanol is dehydrogenated. Reaction conditions can be selected and controlled such that at least 40%, 45%, 50%, 55%, 60%, 65%, 70%, 75%, 80%, 85%, 90%, or 95% of dehydrogenated 2-butanol yields 2-butanone. Reaction conditions can be selected and controlled such that the percent weight yield of MEK from 2-butanol is at least about 65%, 70%, 75%, 80%, 85%, 90%, or 95% (wt/wt), or the percent weight yield of MEK from dehydrogenated 2-butanol is at least about 65%, 70%, 75%, 80%, 85%, 90%, or 95%. Reaction conditions can be selected and controlled such that the coupled dehydrogenation and conversion reactions have selectivity to a desired product greater than 40%, 50%, 60%, 70%, 80%, or 90%, and weight yield greater than 40%, 50%, 60%, 70%, 80%, or 90%. The overall conversion of 2-butanol can be less than 100%, 80%, 60%, or 50%, and the molar yield of the dehydrogenated 2-butanol to MEK can be greater than 80%, 85%, 90%, or 95%.

Figure 3A:
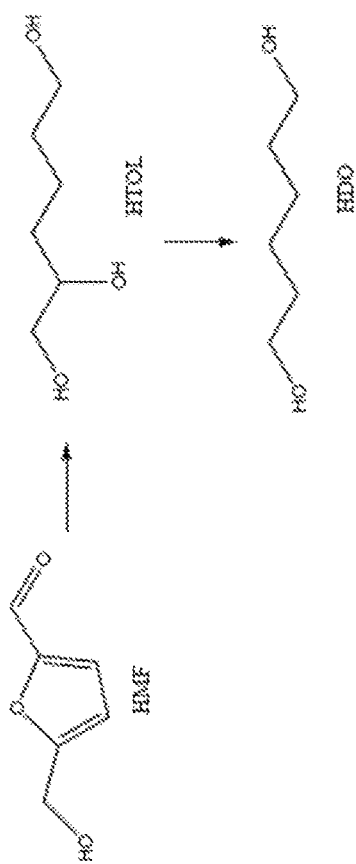
FIG. 3A shows a simplified conversion of 5-(hydroxymethyl)furfural (HMF) to 1,2,6-hexanetriol (HTOL), and the consecutive conversion of HTOL to 1,6-hexanediol (HDO).
Figure 3B:
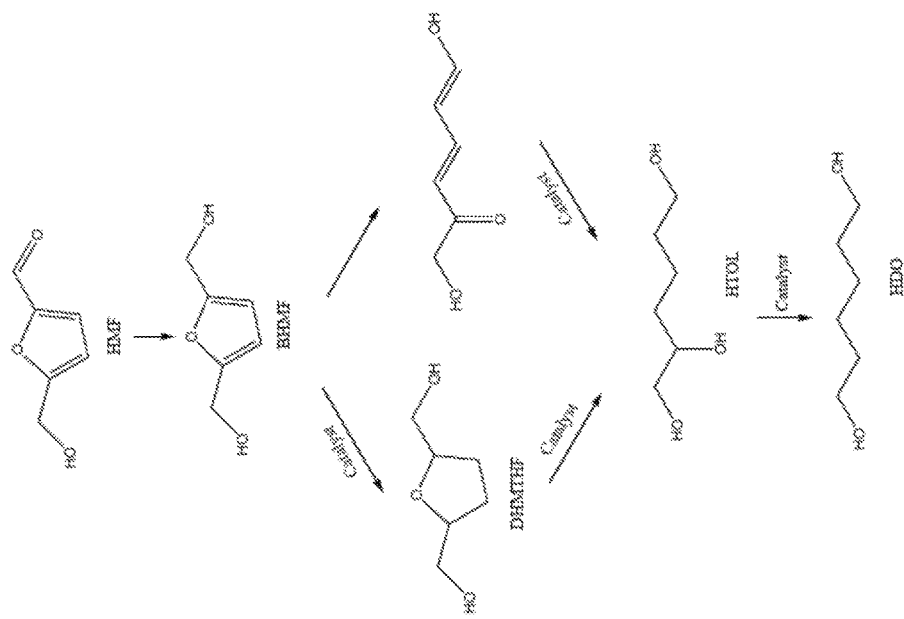
FIG. 3B shows a simplified conversion of HMF to bi-hydroxymethyl furan (BHMF) and the consecutive reactions of BHMF to HTOL and HTOL to HDO.

HMF can be converted in sequential reactions to produce 1,6-hexanediol (HDO). FIG. 3B provides a simplified illustration of the conversion of HMF to HDO. HMF is first hydrogenated to bi-hydroxymethyl furan (BHMF). BHMF is then reacted through hydrogenation and ring opening to HTOL. The intermediate formed during the conversion of BHMF, i.e., HTOL, can be controlled by varying reaction conditions, such as, for example, the use of a catalyst. Finally, HTOL goes through catalytic hydregenolysis to form HDO. At least 40%, 45%, 50%, 55%, 60%, 65%, 70%, 75%, 80%, 85%, 90%, or 95% of the reacted HMF is fully converted to HDO. The conversion of HMF to HDO requires 5 equivalents of 2-butanol converting to MEK, according to the following reaction:

$$5C_4H_{10}O+C_6H_6O_3 \rightarrow 5C_4H_8O+C_6H_{14}O_2+H_2O$$

Suitable catalysts that can be used during the conversion of HMF to HDO include, but are not limited to, Ru/C, Pt/C, $Au/TiO_2$. Any catalyst disclosed herein can be used, or any catalyst known in the art can be used. Additionally, the catalyst can be a metal catalyst selected from palladium, iridium, platinum, ruthenium, nickel, rhodium, scandium, titanium, vanadium, chromium, manganese, iron, cobalt, copper, zinc, yttrium, zirconium, niobium, molybdenum, technetium, silver, cadmium, lanthanum, hafnium, tantalum, tungsten, rhenium, osmium, gold, or mercury. The temperature of the reaction can be selected to provide optimized selectivity for a desired product, as well as a higher rate of 2-butanol dehydrogenation. The temperature of reaction can be greater than about 150, 160, 170, 180, 190, or 200° C.

3. Conversion of Carboxylic Acids and Carboxylic Acid Derivatives

The dehydrogenation of 2-butanol to MEK can be coupled to the conversion of carboxylic acids and carboxylic acid derivatives to various products. As discussed above, the reaction conditions can be selected and controlled such that at least 40%, 45%, 50%, 55%, 60%, 65%, 70%, 75%, 80%, 85%, 90%, or 95% of 2-butanol is dehydrogenated. Reaction conditions can be selected and controlled such that at least 40%, 45%, 50%, 55%, 60%, 65%, 70%, 75%, 80%, 85%, 90%, or 95% of dehydrogenated 2-butanol yields 2-butanone. Reaction conditions can be selected and controlled such that the percent weight yield of MEK from 2-butanol is at least about 65%, 70%, 75%, 80%, 85%, 90%, or 95% (wt/wt), or the percent weight yield of MEK from dehydrogenated 2-butanol is at least about 65%, 70%, 75%, 80%, 85%, 90%, or 95%. Reaction conditions can be selected and controlled such that the coupled dehydrogenation and conversion reactions have selectivity to a desired product greater than 40%, 50%, 60%, 70%, 80%, or 90%, and weight yield greater than 40%, 50%, 60%, 70%, 80%, or 90%. The overall conversion of 2-butanol can be less than 100%, 80%, 60%, or 50%, and the molar yield of the dehydrogenated 2-butanol to MEK can be greater than 80%, 85%, 90%, or 95%.

2,4-dihydroxy butanoic acid can be hydrogenated to 1,4-butanediol directly with a catalyst. Any catalyst disclosed herein can be used, or any catalyst known in the art can be used. Alternatively, 2,4-dihydroxy butanoic acid can be hydrogenated to 1,2,4-butanetriol, and, through a consecutive reaction, to 1,4-butanediol.

The dehydrogenation of 2-butanol to MEK can be coupled to the conversion of 2-hydroxybutanedioic acid (malic acid) or butanedioic acid (succinic acid) to 1,4-butanediol.

Many other carboxylic acids and carboxylic acid derivatives can be converted by coupling with the dehydrogenation of 2-butanediol to MEK.

4. Conversion of Levoglucosenone

The dehydrogenation of 2-butanol to MEK can be coupled to the conversion of levoglucosenone to produce various products. As discussed above, the reaction conditions can be selected and controlled such that at least 40%, 45%, 50%, 55%, 60%, 65%, 70%, 75%, 80%, 85%, 90%, or 95% of 2-butanol is dehydrogenated. Reaction conditions can be selected and controlled such that at least 40%, 45%, 50%, 55%, 60%, 65%, 70%, 75%, 80%, 85%, 90%, or 95% of dehydrogenated 2-butanol yields 2-butanone. Reaction conditions can be selected and controlled such that the percent weight yield of MEK from 2-butanol is at least about 65%, 70%, 75%, 80%, 85%, 90%, or 95% (wt/wt), or the percent weight yield of MEK from dehydrogenated 2-butanol is at least about 65%, 70%, 75%, 80%, 85%, 90%, or 95%. Reaction conditions can be selected and controlled such that the coupled dehydrogenation and conversion reactions have selectivity to a desired product greater than 40%, 50%, 60%, 70%, 80%, or 90%, and weight yield greater than 40%, 50%, 60%, 70%, 80%, or 90%. The overall conversion of 2-butanol can be less than 100%, 80%, 60%, or 50%, and the molar yield of the dehydrogenated 2-butanol to MEK can be greater than 80%, 85%, 90%, or 95%.

For example, levoglucosenone can be hydrogenated to produce levoglucosanol, dihydrolevoglucosenone, 1,6-anhydro-3,4-dideoxy-p-D-pyranose-2-one, 1,2,5,6-tetrahydroxyhexane, tetrahydro-2,5-furandimethanol, 1,2,6-hexanetriol, tetrahydro-2H-pyran-2-methanol, 2-hydroxymethyl-5-hydroxytetrahydro-2H-pyran, tetrahydrofuran 2,5-dimethanol, 2-hydroxymethyltetrahydropyran, 1,2,5,6-tetrahydroxyhexane, 1,2,5-hexanetriol, 2-hydroxymethyl-5hydroxytetrahydropyran, 1,6-hexanediol, 1,2-hexanediol, 1,2-cyclohexanediol, 1,5-hexanediol, 1-hexanol, 1-pentanol, or 1,5-pentanediol.

The conversion reaction can be carried out under reaction conditions as disclosed herein. Any catalyst disclosed herein can be used, or any catalyst known in the art can be used.

Compositions of the Systems, Methods, and Process

Provided herein are compositions. A composition can comprise a conversion product. A composition can be produced by the processing of a biomass or biomass-derived molecule that is converted according to the systems, methods, and processes disclosed herein. A composition can comprise a commercial product. The commercial product can be produced by processing the conversion product. The conversion product can be produced by the conversion of a biomass or biomass-derived molecule according to the systems, methods, and processes disclosed herein.

The commercial product can comprise a polymer, where the polymer can be selected from polyester, polyurethane, polyamide, polycarbonate, polyacetate or epoxy resin, or a combination thereof. A product can comprise at least about 50 ppb, 60 ppb, 70 ppb, 80 ppb, 90 ppb, 100 ppb, 110 ppb, 120 ppb, 130 ppb, 140 ppb, or 150 ppb of a marker molecule, wherein the marker molecule can comprise 2-butanol, 2-butanone, 5-[(1-methylpropoxy)methyl]-2-furancarboxaldehyde, 5-hydroxymethyl-2-[(1-methylpropoxy)methyl]furan, 2-methyl-5-[(1-methylpropoxy)methyl]furan, or 2,5-[bis(1-methylpropoxy)-methyl]furan, or a combination thereof.

EXAMPLES

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims. All publications, patents, and patent applications cited herein are hereby incorporated by reference in their entirety for all purposes.

Example 1

Conversion of Furan to THF

This example describes the coupling of 2-butanol dehydrogenation with the conversion of furan to THF.

Furan was added to 2-butanol and dodecane in a 50 mL stirred Hastelloy reactor (Autoclave Engineering EZE-Seal). Copper chromite and Ni/silica catalysts were used to catalyze the reaction. Nitrogen was used to flush and pressurize the reactor to 200 psi. The mixture was then heated to 160 to 220° C. for 4 to 20 hours in a pressure reactor. After 4 hours, the reactor was cooled in an ice-water bath before opening. The resulting product was analyzed by gas chromatography. The results are summarized in Table 1.

TABLE 1

Hydrogenation of furan to THF with coupled de-hydrogenation of 2-butanol to MEK

| | Conditions | | | | | Reactants, g | | | Products, g | | |
|---|---|---|---|---|---|---|---|---|---|---|---|
| | | | Pressure, | | | | | | | | |
| Ref | T° C. | hours | Psi | Ni/Si | Cu2Cr2O5 | Dodecane | 2-BuOH | Furan | 2-BuOH | MEK | Furan |
| 270114 | 208 | 4 | 450 | 0.15 | 0.22 | 10.02 | 9.88 | 1.99 | 4.53 | 3.79 | 0.15 |
| 280214 | 219 | 4 | 626 | 0.72 | 0.69 | 11.97 | 11.87 | 3.98 | 2.43 | 8.32 | 0.54 |
| 060314 | 165 | 6 | 335 | 0.52 | 0.43 | 9.89 | 10.75 | 4.22 | 8.64 | 2.02 | 2.85 |
| 080314 | 170 | 4.5 | 125 | 0.93 | 0.96 | 10.91 | 9.79 | 4.01 | 5.36 | 4.32 | 2.03 |

| | Products, g | | | Weight | | | | | |
|---|---|---|---|---|---|---|---|---|---|
| | | Furfuryl | Dimethyl | Converstion, % | | Yield, % | | Selectivity, % | |
| Ref | THF | alcohol | furan | 2-BuOH | furan | MEK | THF | MEK | THF |
| 270114 | 0.98 | 0.10 | 0.07 | 54 | 92 | 38 | 49 | 73 | 50 |
| 280214 | 1.51 | 0.44 | 0.14 | 80 | 87 | 70 | 38 | 91 | 41 |
| 060314 | 0.39 | 0.05 | 0.06 | 20 | 33 | 19 | 9 | 99 | 27 |
| 080314 | 1.02 | 0.22 | 0.00 | 45 | 49 | 44 | 25 | 100 | 49 |

Example 2

Conversion Octene to Octane

This example describes the coupling of 2-butanol dehydrogenation with the conversion of octene to octane.

Experiments are conducted to evaluate the efficiency of multiple organosilica catalysts for the dehydrogenation of 2-butanol to MEK by using octene as a reactant. The catalysts tested are $Cu/SiO_2$ (4.7% (wt/wt) Cu), $CuO/SiO_2$ (11.9% (wt/wt) CuO), $Cu_2Cr_2O_5/SiO_2$ (6% (wt/wt) Cu and 5.1% (wt/wt) Cr), and $Pd/SiO_2$. All catalysts are provided by SiliCycle Inc, Quebec City, Canada. To evaluate the recyclability of the catalyst, the washed and dried catalyst is tested in repeated reactions.

The experiments are carried out in a 160 mL PARR Series 5500 High Pressure Compact Laboratory Reactor. The reactor is loaded with 30 g of 100-50% 2-butanol/dodecane, 1.5 g octene, and 0.17 g catalyst. Nitrogen is added to yield pressures ranging from between 200 to 400 psi at room temperature. The reactions are conducted at multiple temperatures, which range from 180 to 240° C. The reaction time is controlled, and the reactions are conducted for multiple time periods, ranging from 4 to 24 hours.

Samples of the liquid phase are analyzed by gas chromatography in order to determine the concentration of 2-butanol, MEK, octene, and octane, as well as to identify and quantify any other products formed in the reaction. The liquid phase is analyzed by inductively coupled plasma techniques to detect leached metal.

The liquid phase is filtered at the end of the reaction to collect the solid catalyst. At least 80% of the 2-butanol is converted to MEK, while hydrogenating octene to octane.

Example 3

Conversion of HMF to HDO

This example describes the coupling of 2-butanol dehydrogenation with the conversion of HMF to HDO.

Experiments are conducted to evaluate the efficacy of supported metal catalysts for the catalytic conversion of HMF to HDO. The catalysts tested are $Cu/SiO_2$ (4.7% (wt/wt) Cu), $CuO/SiO_2$ (11.9% (wt/wt) CuO), $Cu_2Cr_2O_5/SiO_2$ (6% (wt/wt) Cu and 5.1% (wt/wt) Cr), and $Pd/SiO_2$, as well as a combination of a copper-based catalyst and a palladium-based catalyst. All catalysts are provided by SiliCycle Inc, Quebec City, Canada. To evaluate the recyclability of the catalyst, the washed and dried catalyst is tested in repeated reactions.

The reactions are carried out in a 160 mL PARR Series 5500 High Pressure Compact Laboratory Reactor. The reactor is loaded with 30 g of 100-50% 2-butanol/dodecane, 1.5 g octene, and 0.17 g catalyst. Nitrogen is added to pressures ranging from between 200 to 400 psi at room temperature. The reactions are conducted at multiple temperatures, which range from 180 to 240° C. The reaction time is controlled, and the reactions are conducted for multiple time periods, ranging from 4 to 24 hours.

Samples of the liquid phase are analyzed by gas chromatography to determine the concentration of 2-butanol, MEK, HMF, BHMF, 1,2,6-hexanetriol, and HDO, as well as to identify and quantify any other intermediates or products formed in the reaction. The liquid phase is analyzed by inductively coupled plasma techniques to detect leached metal.

The liquid phase is filtered at the end of the reaction to collect the solid catalyst. At least 80% of the 2-butanol is converted to MEK, while hydrogenating HMF to HDO.

What is claimed is:

1. A method for producing 2-butanone and a conversion product, the method comprising:
   dehydrogenating 2-butanol to yield 2-butanone, thereby releasing hydrogen;
   using hydrogen released from the dehydrogenating in a conversion reaction, wherein the conversion reaction converts a biomass-derived molecule to a conversion product; and
   recovering 2-butanone and the conversion product.

2. The method of claim 1, wherein the biomass-derived molecule is derived from lignocellulosic biomass.

3. The method of claim 2, wherein the biomass-derived molecule is selected from a saccharide, a dehydrated saccharide, a halodehydrated saccharide, a dehydrated and partially-hydrogenated saccharide, and a hydrogenated saccharide, or a combination thereof.

4. The method of claim 1, wherein the biomass-derived molecule is selected from a monosaccharide, an oligosaccharide, furfural, halofurfural, methyl furfural, furfuryl alcohol, methyl furfuryl alcohol, (methoxymethyl)-methyl furfural, hydroxymethylfurfural, 2-methylfuran, dimethylfuran, 2,5-bis(hydroxymethyl)furan, 5-hydroxymethyl-2-[(1-methylethoxy)methyl] furan, 2-methyl-5[(1-methylmethoxy)methyl] furan, bis(1-methoxyethoxy)-methyl furan, tetrahydrofuran, levoglucosenone, 1,2,6-hexanetriol, 1,2,5-pentanetriol, 1,2,4-butanetriol, 2,4-dihydroxy butanoic acid, 2,4-hydroxybutanoic acid, succinic acid, malic acid, maleic acid, xylitol, mannitol, sorbitol, erythritol, arabitol, and galactitol, or a combination thereof.

5. The method of claim 4, wherein the biomass-derived molecule is selected from furfural, hydroxymethylfurfural, and 2,4-hydroxybutanoic acid.

6. The method of claim 1, wherein the conversion product is selected from 1,6-hexanediol, 1,4-butanediol, 1,5-pentanediol, hexanetriol, 1,2,4-butanetriol, 2-methyl furan, furfuryl alcohol, tetrahydrofuran, bi-hydroxymethyl furan, 5-[(1-methylpropoxy)methyl]-2-furancarboxaldehyde, 5-hydroxymethyl-2-[(1-methylpropoxy)methyl]furan, 2-methyl-5-[(1-methylpropoxy)methyl]furan, and 2,5-[bis(1-methylpropoxy)methyl]furan.

7. The method of claim 6, wherein the conversion product is selected from 1,6-hexanediol, 1,4-butanediol, and 1,5-pentanediol.

8. The method of claim 1, further comprising diluting the 2-butanol with a solvent, wherein the solvent is inert in the conversion reaction.

9. The method of claim 8, wherein the solvent comprises a $C_4$-$C_{18}$ hydrocarbon.

10. The method of claim 1, further comprising catalyzing the dehydrogenating or the conversion reaction with a catalyst.

11. The method of claim 10, wherein the catalyst is selected from a copper-based catalyst, a Raney nickel-based catalyst, a metal-containing organosilica-based catalyst, and an iridium complex-based catalyst, or a combination thereof.

12. The method of claim 10, further comprising a co-catalyst, an enhancer, a promoter, or a combination thereof.

13. The method of claim 1, wherein the conversion reaction comprises conversion of furfural to 1,5-pentanediol.

14. The method of claim 1, wherein the conversion reaction comprises conversion of hydroxymethylfurfural to 1,6-hexanediol.

15. The method of claim 1, wherein the conversion reaction comprises conversion of 2,4-hydroxybutanoic acid to 1,4-butanediol.

16. The method of claim 1, wherein the dehydrogenating and the conversion reaction occur in the same reaction vessel.

17. The method of claim 1, wherein the dehydrogenating and the conversion reaction occur in more than one reaction vessels, wherein the more than one reaction vessels are functionally connected either continuously or discontinuously.

18. The method of claim 1, wherein at least 40% of the 2-butanol is dehydrogenated.

19. A reaction mixture comprising:
2-butanol;
2-butanone;
a biomass-derived molecule; and
a conversion product,
wherein the conversion product is obtainable from a conversion reaction of the biomass-derived molecule, and wherein the conversion reaction comprises hydrogenation, hydrogenolysis, or hydrodeoxygenation.

20. The reaction mixture of claim 19, wherein the biomass-derived molecule is derived from lignocellulosic biomass.

21. The reaction mixture of claim 19, wherein the biomass-derived molecule is selected from a saccharide, a dehydrated saccharide, a halodehydrated saccharide, a dehydrated and partially-hydrogenated saccharide, and a hydrogenated saccharide, or a combination thereof.

22. The reaction mixture of claim 19, wherein the biomass-derived molecule is selected from furfural, hydroxymethylfurfural, and 2,4-hydroxybutanoic acid.

23. The reaction mixture of claim 19, further comprising an inert solvent.

24. The reaction mixture of claim 23, wherein the inert solvent is selected from hexane, cyclohexane, heptane, octane, decane, and dodecane, or a combination thereof.

25. The reaction mixture of claim 19, further comprising a catalyst.

26. The reaction mixture of claim 19, further comprising hydrogen.

27. The reaction mixture of claim 19, wherein the conversion product is selected from 1,6-hexanediol, 1,4-butanediol, 1,5-pentanediol, hexanetriol, 1,2,4-butanetriol, 2-methyl furan, furfuryl alcohol, tetrahydrofuran, bi-hydroxymethyl furan, 5-[(1-methylpropoxy)methyl]-2-furancarboxaldehyde, 5-hydroxymethyl-2-[(1-methylpropoxy)methyl]furan, 2-methyl-5-[(1-methylpropoxy)methyl]furan, and 2,5-[bis(1-methylpropoxy)methyl]furan, or a combination thereof.

28. The reaction mixture of claim 19, wherein the conversion product is selected from 1,6-hexanediol, 1,4-butanediol, and 1,5-pentanediol.

29. The reaction mixture of claim 19, wherein the 2-butanol, 2-butanone, biomass-derived molecule, and conversion product are in the same reaction vessel.

30. The reaction mixture of claim 19, wherein the 2-butanol and 2-butanone are in a different reaction vessel than the biomass-derived molecule and conversion product, and wherein the reaction vessels are functionally connected either continuously or discontinuously.

* * * * *